United States Patent
DeAngelis et al.

(10) Patent No.: US 10,273,517 B2
(45) Date of Patent: *Apr. 30, 2019

(54) METHODS OF PRODUCING TESTOSTERONAN POLYMERS USING TESTOSTERONAN SYNTHASE

(71) Applicant: The Board of Regents of the University of Oklahoma, Norman, OK (US)

(72) Inventors: Paul L. DeAngelis, Edmond, OK (US); Nigel J. Otto, Santa Fe, NM (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,860

(22) Filed: May 15, 2017

(65) Prior Publication Data

US 2017/0247732 A1    Aug. 31, 2017

Related U.S. Application Data

(63) Continuation of application No. 13/981,886, filed as application No. PCT/US2012/023351 on Jan. 13, 2012, now Pat. No. 9,695,427.

(60) Provisional application No. 61/437,805, filed on Jan. 31, 2011.

(51) Int. Cl.
```
C12P 19/04    (2006.01)
C12P 19/26    (2006.01)
C08B 37/00    (2006.01)
C12N 9/04     (2006.01)
C12N 9/10     (2006.01)
C12N 9/12     (2006.01)
C12N 15/52    (2006.01)
```

(52) U.S. Cl.
CPC .......... *C12P 19/26* (2013.01); *C08B 37/0063* (2013.01); *C12N 9/0006* (2013.01); *C12N 9/1051* (2013.01); *C12N 9/1241* (2013.01); *C12N 15/52* (2013.01); *C12P 19/04* (2013.01); *C12Y 101/01022* (2013.01); *C12Y 207/07009* (2013.01)

(58) Field of Classification Search
CPC ..... C12P 19/26; C12N 9/1051; C12N 9/1241; C12N 9/0006; C12N 15/52; C12Y 101/01022; C12Y 207/07009; C08B 37/0063

See application file for complete search history.

(56) References Cited

U.S. PATENT DOCUMENTS 6,423,514 B1    7/2002  Briskin
6,444,447 B1    9/2002  DeAngelis
6,492,150 B1   12/2002  McDonald et al.

OTHER PUBLICATIONS

Ausubel, F., Current Protocols in Molecular Biology, Hybridization Analysis of DNA Blots, pp. 2.10.8-2.10.11, 1993.*
Branden et al., Introduction to Protein Structure, Garland Publishing Inc., New York, p. 247.*
Witkowski et al., Biochemistry 38:11643-11650, 1999.*
Seffernick et al., J. Bacteriol. 183(8):2405-2410, 2001.*
Sadowski et al., Current Opinion in Structural Biology 19:357-362, 2009.*
Schleheck et al., GenBank accession No. EED66922, Jan. 14, 2009.*
Schleheck et al., GenBank accession No. AAUJ0200000, Jan. 14, 2009.*
Florin et al., Journal of Bacteriology 178(11):3322-3330, 1996.*
Anderson et al., The Journal of Biological Chemistry 268(26):19858-19865, 1993.*
Sugiura et al., The Journal of Biological Chemistry 285(3):1597-1606, 2010.*
Wendland et al., Applied and Environmental Microbiology 75(18):5840-5845, 2009.*
YMDB16123, Yeast Metabolome Database 2.0, accessed Nov. 22, 2017.*
Otto, et al.; "Comamonas Testosteronan Synthase, a Bifunctional Glycosyltransferase That Produces a Unique Heparosan Polysaccharide Analog," Glycobiology (2011), vol. 21, No. 10, pp. 1331-1340.
Volpi; "Purification of the *Escherichia coli* K5 Capsular Polysaccharide and Use of High-Performance Capillary Electrophoresis to Qualitative and Quantitative Monitor the Process," Electrophoresis (2004), vol. 25, No. 18-19, pp. 3307-3312.
Vann, et al.; "The Structure of the Capsular Polysaccharide (K5 Antigen) of Urinary-Tract-Infective *Eschericia coli* 010: K5LH4," Eur. J. Biochem. (1981) vol. 116, pp. 359-364.
Sismey-Ragatz, et al.; "Chemoenzymatic Synthesis with District Pasteurella Heparosan Synthases," J. Biol. Chem. (2007), vol. 282, No. 29, pp. 28321-28327.

* cited by examiner

*Primary Examiner* — Delia M Ramirez
(74) *Attorney, Agent, or Firm* — Dunlap Codding, P.C.

(57) ABSTRACT

Testosteronan, a heparosan analog having the structure [-4-D-GlcUA-α1,4-D-GlcNAc-α1-]$_n$, is produced by testosteronan synthase, a single protein that is a dual-action catalyst that utilizes UDP-GlcUA and UDP-GlcNAc to synthesize a polysaccharide having the structure [-4-D-GlcUA-α1,4-D-GlcNAc-α1-]$_n$.

15 Claims, 13 Drawing Sheets
(8 of 13 Drawing Sheet(s) Filed in Color)
Specification includes a Sequence Listing.

A.

B.

Hyaluronan

Heparosan

Testosteronan

METHODS OF PRODUCING TESTOSTERONAN POLYMERS USING TESTOSTERONAN SYNTHASE

CROSS REFERENCE TO RELATED APPLICATIONS

This application is a continuation of U.S. Ser. No. 13/981,886, filed Jul. 25, 2013 now U.S. Pat. No. 9,695,427, issued Jul. 4, 2017; which is a US national stage application filed under 35 USC § 371 of International Application No. PCT/US12/23351, filed Jan. 31, 2012; which claims benefit under 35 USC § 119(e) of provisional application U.S. Ser. No. 61/437,805, filed Jan. 31, 2011. The entire contents of the above-referenced patents and patent applications are hereby expressly incorporated herein by reference.

STATEMENT REGARDING FEDERALLY FUNDED RESEARCH OR DEVELOPMENT

This invention was made with government support under Contract Number HL062244 awarded by the National Institutes of Health. The government has certain rights in the invention.

BACKGROUND OF THE INVENTION

1. Field of the Invention

The presently claimed and disclosed inventive concept(s) relates, in general, to heparosan analogs, as well as the synthases responsible for production of said heparosan analogs. The presently disclosed and claimed inventive concept(s) is also related to methods of production and use of the heparosan analogs and the heparosan analog synthases.

2. Brief Description of the Related Art

Certain pathogenic microbes employ extracellular capsules of host-like glycans to evade host defenses and to increase virulence. Previous work by the inventors and others has identified very distinct types of microbial glycosaminoglycan [GAG] synthases, the bifunctional enzymes that assemble GAG polysaccharides. These synthases include peripheral membrane-associated two domain enzymes such as the *Pasteurella multocida* GAG synthases PmHAS (hyaluronan) (DeAngelis et al., 1996 and 1998), PmCS (chondroitin) (DeAngelis et al., 2000), PmHS1 and PmHS2 (heparosan) (DeAngelis et al., 2002 and 2004) (FIG. 1) and KfoC (chondroitin) from *Escherichia coli* K4 (Ninomiya et al., 2002), as well as integral membrane proteins with unknown domain structures such as the *Streptococcus pyogenes* hyaluronan synthase SpHAS (DeAngelis et al., 1993) and the Chlorella virus PBCV-1 hyaluronan synthase CvHAS (DeAngelis et al., 1997). All of the known GAG synthases employ UDP-sugar precursors to form the repeating disaccharide units (DeAngelis, 2002). The *Streptococcus* hyaluronan synthase has some similarity to vertebrate hyaluronan synthases at the amino acid sequence level (Weigel et al., 2007), but the bacterial chondroitin and heparosan synthases are quite different to their vertebrate counterparts (DeAngelis et al., 2000 and 2002).

*Comomonas testosteroni* (Ct) is a Gram-negative aerobic bacteria that is found in diverse environments (Ma et al., 2009). Bacteria of the genus *Comamonas* are predominant in activated sewage sludge (Dias et al., 1964) and are defined by a poor ability to use carbohydrates; instead carbon is derived from molecules such as testosterone and other cyclic hydrocarbons (Horinouchi et al., 2010; Linares et al., 2008). *C. testosteroni* has recently been identified as an opportunistic human pathogen that has been found in various hospital infections including meningitis (Arda et al., 2003; Jin et al., 2008), bacteremia (Gul et al., 2007), and endophthalmitis (Reddy et al., 2009). The ability for *C. testosteroni* to survive and thrive in such diverse environments, as well as its potential use for cleaning up environmental contamination with xenobiotic compounds such as polychlorinated biphenyls and linear alkylbenzenesulfonate make it a particularly interesting organism (Schleheck et al., 2004 and 2010). There is only one published study indicating the presence of a mucoid exopolysaccharide capsule of *C. testosteroni* A20 (Bossier et al., 1996); however, there is no genomic information available for this strain, and the nature of the polysaccharide was not determined.

Heparin is a useful drug widely used in hospitals as an anticoagulant. Heparin also has other potential uses in combating diseases such as cancer and inflammation, but the polysaccharide's anticoagulant effects make it difficult to use for these other promising indications (i.e., patients may have excessive bleeding). Also, heparin is currently derived from animal products (e.g., porcine intestinal mucosa, bovine lung); thus, its method of preparation must remove adventitious agents, antigens, etc., and its potency is variable. In addition, due to collection of almost all pigs slaughtered around the world for food, the supply chain is not secure, as evidenced by the contaminated heparin from China in 2008 that resulted in many deaths. Therefore, microbial-derived heparin substitutes are desirable; however, the manufacture using heparosan (unsulfated, unepimerized backbone of heparin) as the precursor for heparin requires many steps to convert into heparin or heparin-like material.

Thus, there is a need in the art for new non-animal-derived heparosan analogs that may be simpler to convert into anticoagulants or other therapeutics.

DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PRESENTLY DISCLOSED AND CLAIMED INVENTIVE CONCEPT(S)

Figure 1:
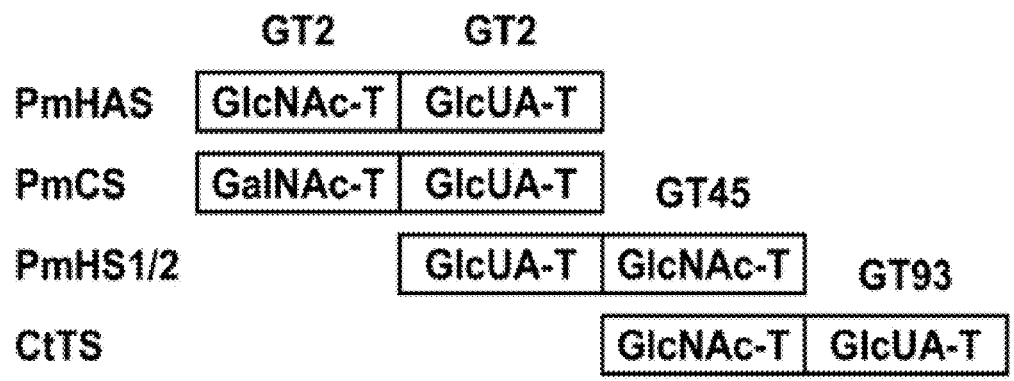
FIG. 1 illustrates a schematic alignment of the bifunctional *Pasteurella* glycosaminoglycan synthases with the *Comamonas testosteronan* synthase and their GAG products. Panel A—The PmHS GT45 domain is 32% identical to that of the *Comamonas* synthase (CtTS). There are only 8 predicted members of the GT45 family. Bioinformatic analyses of the putative GlcUA transferase domain of the *Comamonas* synthase indicate that this is a new CAZy GT family member designated GT93. Panel B—The GAG repeat disaccharide structures of HA, heparosan and testosteronan are shown as Haworth structures; these GAGs all possess the same monosaccharide units, but in different glycosidic linkages. (note: chondroitin has the same structure as HA, but with a GalNAc unit substituting for GlcNAc).
Figure 1:
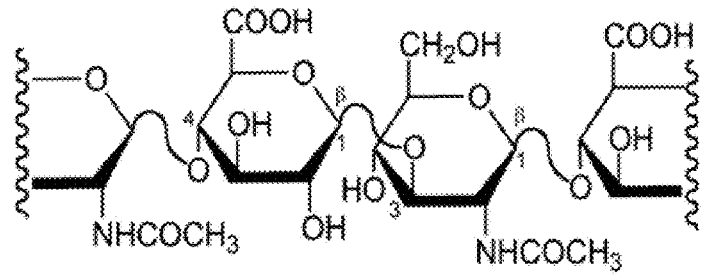
Figure 1:
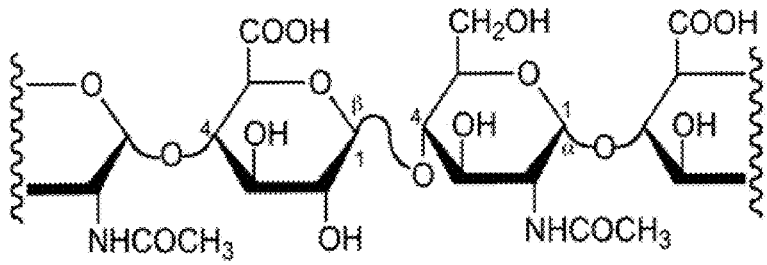
Figure 1:
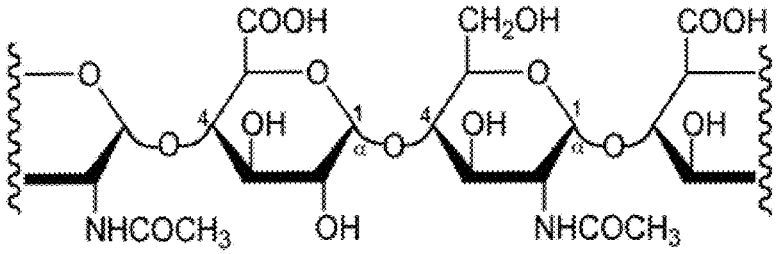

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "isolated" as used herein means that a biological material, such as but not limited to a nucleic acid or protein, has been removed from its original environment in which it is naturally present. For example, a polynucleotide present in a plant, mammal or animal is present in its natural state and is not considered to be isolated. The same polynucleotide separated from the adjacent nucleic acid sequences in which it is naturally inserted in the genome of the plant or animal is considered as being "isolated".

The term "isolated" is not meant to exclude artificial or synthetic mixtures with other compounds, or the presence of impurities which do not interfere with the biological activity and which may be present, for example, due to incomplete purification, addition of stabilizers or mixtures with pharmaceutically acceptable excipients, and the like.

"Isolated polypeptide" or "isolated protein" as used herein means a polypeptide or protein which is substantially free of those compounds that are normally associated with the polypeptide or protein in a natural state, including but not limited to, other proteins or polypeptides, nucleic acids, carbohydrates, lipids and the like.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The term "variant" as used herein when referring to, for example, polynucleotides encoding a polypeptide variant of a given reference polypeptide, are polynucleotides that differ from the reference polypeptide but generally maintain their functional characteristics of the reference polypeptide. A variant of a polynucleotide may be a naturally occurring allelic variant or may be a variant that is not known to occur naturally. Such non-naturally occurring variants of the reference polynucleotide can be made by, for example but by way of limitation, mutagenesis techniques, including those mutagenesis techniques that are applied to polynucleotides, cells or organisms.

As used herein, the terms "nucleic acid segment", "nucleic acid sequence", "nucleotide segment", "nucleotide sequence", "DNA sequence" and "DNA segment" are used interchangeably and refer to a DNA molecule which has been isolated free of total genomic DNA of a particular species. Therefore, a "purified" or "isolated" nucleotide sequence as used herein refers to a DNA segment which contains a testosteronan synthase ("TS") coding sequence yet is isolated away from, or purified free from, unrelated genomic DNA, for example but by way of limitation, total *Comomonas testosteroni* or host genomic DNA. Included within these terms are DNA segments and smaller fragments of such segments, and also recombinant vectors including, for example, plasmids, cosmids, phage, viruses, and the like.

Similarly, a DNA segment comprising an isolated or purified CtTS gene refers to a DNA segment including TS coding sequences isolated substantially away from other naturally occurring genes or protein encoding sequences. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest, in this case CtTS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

In certain embodiments, DNA sequences in accordance with the presently disclosed and claimed inventive concept(s) will further include genetic control regions which allow the expression of the sequence in a selected recombinant host. Of course, the nature of the control region employed will generally vary depending on the particular use (e.g., cloning host) envisioned.

The term "polysaccharide" as used herein will be understood to refer to large carbohydrate molecules comprising from about 25 sugar units to thousands of sugar units. The term "oligosaccharide" as used herein will be understood to refer to smaller carbohydrate molecules comprising less than about 25 sugar units. The term "polymer" as used herein will be understood to refer to naturally occurring or synthetic compounds that are made up of repeated units. The term "polymer" encompasses both oligosaccharide and polysaccharide structures.

The term "polydisperse" as used herein refers to a polymer having chain lengths that vary over a wide range of molecular masses such that there is molecular-weight non-homogeneity. The term "monodisperse" as used herein will be understood to refer to defined glycosaminoglycan polymers that have a very narrow size distribution. The term "substantially monodisperse" is defined in greater detail herein below. In addition, a polydispersity value or heterogeneity index is a measure of the distribution of molecular mass in a given polymer sample. The calculated polydispersity value is the weight average molecular weight divided by the number average molecular weight; it indicates the distribution of individual molecular masses in a batch of polymers. The polydispersity value has a value equal to or greater than 1, but as the polymer chains approach uniform chain length, the polydispersity value approaches unity.

The term "GlcNAc" refers to N-acetylglucosamine; the terms "GlcA" and "GlcUA" are used herein interchangeably and refer to glucuronic acid. The terms "UDP-GlcNAc" and "UDP-GlcUA" refer to uridine diphosphate sugar precursors of GlcNAc and GlcUA, respectively. These compounds are used by glycosyltransferases to transfer GlcNAc/GlcUA residues to substrates.

Turning now to particular embodiments of the presently claimed and disclosed inventive concept(s), an isolated nucleotide sequence encoding an enzymatically active testosteronan synthase is provided. Testosteronan synthase is a single protein that is a dual-action catalyst that utilizes UDP-GlcUA and UDP-GlcNAc to synthesize a polymer having the repeat structure [-4-D-GlcUA-α1,4-D-GlcNAc-α1-]$_n$. In certain embodiments, the isolated nucleotide sequence encodes CtTs, which comprises the amino acid sequence of SEQ ID NO:1 (assigned GenBank Accession No. ZP_03542636) and is encoded by the nucleotide sequence of SEQ ID NO:2 (residues 2,026,807 to 2,028,729 of GenBank Accession No. NZ_AAUJ02000001.1). As of the filing date of the subject application, the NCBI database contains annotations on Accession No. ZP_03542636 that state that this is a "predicted, hypothetical protein" and that "[t]his record has not been reviewed and the function is unknown".

The scope of the presently disclosed and claimed inventive concept(s) also includes biologically functional equivalents of the sequences disclosed herein above, so long as said equivalents encode testosteronan synthase, the single protein that is a dual-action catalyst that utilizes UDP-GlcUA and UDP-GlcNAc to synthesize a polymer having the repeat structure [-4-D-GlcUA-α1,4-D-GlcNAc-α1-]$_n$. For example, the isolated nucleotide sequence may be at least a certain percentage identical to SEQ ID NO:2 (percent identity being described in greater detail herein below), or encode an amino acid sequence that is at least a certain percentage identical to SEQ ID NO:1. In addition, the isolated nucleotide sequence may be capable of hybridizing to a complement of SEQ ID NO:2 (or to a complement of a nucleotide sequence encoding the amino acid sequence of SEQ ID NO:1) under standard and/or stringent hybridization conditions (as described in greater detail herein below). Further, the isolated nucleotide sequence may encode an amino acid sequence having up to 50 (such as but not limited to, up to 45, 40, 35, 30, 25, 20, 15, 14, 13, 12, 11, 10, 9, 8, 7, 6 or 5) amino acid insertions, deletions or substitutions when compared to SEQ ID NO:1.

The term "a sequence essentially as set forth in SEQ ID NO:1" means that the sequence substantially corresponds to a portion of SEQ ID NO:1 and has relatively few amino acids which are not identical to, or a biologically functional equivalent of, the amino acids of SEQ ID NO:1. The term "biologically functional equivalent" is well understood to those of skill in the art and is embodied in the knowledge that modifications and changes may be made in the structure of a protein or peptide and still obtain a molecule having like or otherwise desirable characteristics. However, it is also well understood by skilled artisans that, inherent in the definition of a biologically functional equivalent protein or peptide, is the concept that there is a limit to the number of changes that may be made within a defined portion of the molecule and still result in a molecule with an acceptable level of equivalent biological activity, and that key active site or structurally vital residues cannot be exchanged (see for example, U.S. Pat. No. 6,355,619, issued to Miller et al. on Mar. 12, 2002, the contents of which are hereby expressly incorporated herein by reference). The term "biologically functional equivalent" is further defined in detail herein as a gene encoding an amino acid sequence essentially as set forth in SEQ ID NO:1, and that is associated with the ability of prokaryotes to produce testosteronan or a "testosteronan-like" (or testosteronan-based) polymer or a testosteronan synthase polypeptide.

One of ordinary skill in the art would appreciate that a nucleic acid segment encoding enzymatically active testosteronan synthase may contain conserved or semi-conserved amino acid substitutions, insertions or deletions to the sequence set forth in SEQ ID NO:1 and yet still be within the scope of the presently disclosed and claimed inventive concept(s). In particular, the art is replete with examples of practitioner's ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019-1029 (1988) [" . . . according to the observed exchangeability of amino acid side chains, only four groups could be delineated; (I) Ile and Val; (ii) Leu and Met; (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . " compatible changes can be made]. Each of these articles, to the extent that they provide additional details to one of ordinary skill in the art in the methods of making such conserved or semi-conserved amino acid substitutions, are hereby expressly incorporated herein in their entirety as though set forth herein. These references and countless others available to one of ordinary skill in the art, indicate that given a nucleic acid sequence, one of ordinary skill in the art could make substitutions and changes to the nucleic acid sequence without changing its functionality.

One of ordinary skill in the art would also appreciate that substitutions can be made to the ctTS nucleic acid segment listed in SEQ ID NO:2 without affecting the amino acid sequence it encodes or result in conservative or semi-conservative substitutions in the amino acid sequence it encodes; therefore, such substituted nucleic acid segments also fall within the scope and claims of the presently disclosed and claimed inventive concept(s). Standardized and accepted functionally equivalent amino acid substitutions are presented in Table 1.

TABLE 1

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Serine, Threonine, Cysteine, Asparagine, Glutamine |
| Negatively Charged R Groups | Aspartic Acid, Glutamic Acid |
| Positively Charged R Groups | Lysine, Arginine, Histidine |

In certain other embodiments, the presently disclosed and claimed inventive concept(s) concerns isolated DNA segments and recombinant vectors that include within their sequence a nucleic acid sequence essentially as set forth in SEQ ID NO:2. The term "essentially as set forth in SEQ ID NO:2" is used in the same sense as described above with respect to the amino acid sequences and means that the nucleic acid sequence substantially corresponds to a portion of SEQ ID NO:2, and has relatively few codons that are not identical, or functionally equivalent, to the codons of SEQ ID NO:2 and encodes a enzymatically active TS or single-action fragment of TS. The term "functionally equivalent codon" is used herein to refer to codons that encode the same amino acid, such as the six codons for arginine or serine, and also refers to codons that encode biologically equivalent amino acids. The term "Biologically Equivalent Amino Acids" refers to residues that have similar chemical or physical properties that may be easily interchanged for one another (as shown in Table I).

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzymatic activity is concerned. The addition of terminal sequences particularly applies to nucleic acid sequences which may, for example, include various non-coding sequences flanking either of the 5' or 3' portions of the coding region or may include various internal sequences, which are known to occur within genes.

Likewise, deletion of certain portions of the TS polypeptide can be desirable. For example, functional truncated versions of pmHAS, the *Pasteurella* hyaluronan synthase, missing the carboxyl terminus enhances the utility for in vitro use. The truncated pmHAS enzyme is a soluble protein that is easy to purify in contrast to the full-length protein (972 residues). Also, the expression level of the enzyme increases greatly as the membrane is not overloaded.

Allowing for the degeneracy of the genetic code as well as conserved and semi-conserved substitutions, sequences which have between about 40% and about 80%; or more preferably, between about 80% and about 90%; or even more preferably, between about 90% and about 99% of nucleotides which are identical to the nucleotide sequence of SEQ ID NO:2 will be sequences which are "essentially as set forth in SEQ ID NO:2". In one embodiment, the sequences will be 40%-42% identical, 42%-44% identical, 44%-46% identical, 46%-48% identical, 48%-50% identical, 50%-52% identical, 52%-54% identical, 54%-56% identical, 56%-58% identical, 58%-60% identical, 60%-62% identical, 62%-64% identical, 64%-66% identical, 66%-68% identical, 68%-70% identical, 70%-72% identical, 72%-74% identical, 74%-76% identical, 76%-78% identical, 78%-80% identical, 80%-82% identical, 82%-84% identical, 84%-86% identical, 86%-88% identical, 88%-90% identical, 90%-92% identical, 92%-94% identical, 94%-96% identical, 96%-98% identical, or 98%-100% identical to SEQ ID NO:2. Sequences which are essentially the same as those set forth in SEQ ID NO:2 may also be functionally defined as sequences which are capable of hybridizing to a nucleic acid segment containing the complement of SEQ ID NO:2 under standard or stringent hybridization conditions. Suitable standard hybridization conditions will be well known to those of skill in the art and are clearly set forth herein below. As certain domains and active sites are formed from a relatively small portion of the total polypeptide, these regions of sequence identity or similarity may be present only in portions of the gene. Additionally, sequences which are "essentially as set forth in SEQ ID NO:1" will include those amino acid sequences that have at least one of the testosteronan enzyme amino acid motifs (described hereinafter in detail) and that also retain the functionality of an enzymatically active TS or single-action fragment thereof.

The polypeptides of the presently disclosed and claimed inventive concept(s) have at least 20%, such as at least 25%, 30%, 40%, 45%, 50%, 55%, 60%, 65%, 70%, 75%, 80%, 90%, or 95% of the TS activity of the mature polypeptide of SEQ ID NO:1.

As is well known to those of ordinary skill in the art, most of the amino acids in a protein are present to form the "scaffolding" or general environment of the protein. The actual working parts responsible for the specific desired catalysis are usually a series of small domains or motifs. Thus, a pair of enzymes that possess the same or similar motifs would be expected to possess the same or similar catalytic activity, thus they are functionally equivalent. Utility for this hypothetical pair of enzymes may be considered interchangeable unless one member of the pair has a subset of distinct, useful properties. Similarly, certain non-critical motifs or domains may be dissected from the original, naturally occurring protein and function will not be affected; removal of non-critical residues does not perturb the important action of the remaining critical motifs or domains. By analogy, with sufficient planning and knowledge, it is possible to translocate motifs or domains from one enzyme to another polypeptide to confer the new enzyme with desirable characteristics intrinsic to the domain or motif. Such motifs for TS are disclosed in particularly hereinafter.

Similarly, certain critical motifs or domains may be changed (mutated) or dissected from the original, naturally occurring protein to thereby affect function; removal of critical residues will perturb the important action of the remaining critical motifs or domains. Such motifs for TS are disclosed in particularly hereinafter. The CtTS enzyme in its natural state is a dual action enzyme with two separate active sites or domains. Theoretically, if the sites are relatively functionally independent, then the alteration of one site or domain will not destroy the activity of the other unmutated site. Therefore, mutated, single-action testosteronan transferases fall within the scope of the presently claimed and disclosed presently disclosed and claimed inventive concept(s).

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents such as formamide and dimethyl sulfoxide, the length of the segments that are hybridizing, and the like. Hybridization may involve the use of shorter nucleic acid segments for hybridization, for example fragments between about 14 and about 100 nucleotides, as well as larger nucleic acid segments, for example, up to the entire length of SEQ ID NO:2. When shorter nucleic acid segments are utilized, exemplary salt and temperature conditions for overnight standard hybridization may include 1.2×-1.8× HPB (High Phosphate Buffer) at 40-50° C. or 5×SSC (Standard Saline Citrate) at 50° C. Washes in low salt (10 mM salt or 0.1×SSC) are used for stringent hybridizations with room temperature incubations of 10-60 minutes. Washes with 0.5× to 1×SSC, 1% Sodium dodecyl sulfate at room temperature are used in lower stringency washes for 15-30 minutes. For all hybridizations, 1×HPB=0.5 M NaCl, 0.1 M $Na_2HPO_4$, 5 mM EDTA, pH 7.0, and 20×SSC=3 M NaCl, 0.3 M Sodium Citrate with pH 7.0.

For long probes of at least 100 nucleotides in length, stringent conditions are defined as prehybridization and hybridization at 42° C. in 5×SSPE, 0.3% SDS, 200 mg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The nucleic acid segments of the presently disclosed and claimed inventive concept(s), regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. For example, functional spHAS-(Histidine)$_6$ and x1HAS1-(Green Fluorescent Protein) fusion proteins have been reported. It is therefore contemplated that a nucleic acid fragment of almost any length may be employed, with the total length preferably being limited by the ease of preparation and use in the intended recombinant DNA protocol.

Another embodiment of the presently disclosed and claimed inventive concept(s) is a recombinant vector comprising at least one of the isolated nucleotide sequences encoding an enzymatically active testosteronan synthase described herein above. As used herein, the term "recombinant vector" refers to a vector that has been modified to contain a nucleotide sequence (or multiple nucleotide sequences, such as but not limited to, two or more copies of SEQ ID NO:2) that encodes a TS protein, or fragment thereof. The recombinant vector may be further defined as an expression vector comprising one or more promoters operatively linked to said TS-encoding nucleotide sequence. Examples of vectors that may be utilized in accordance with the presently disclosed and claimed inventive concept(s) include, but are not limited to, plasmids, cosmids, phage, integrated cassettes, virus vectors, combinations thereof, and any other similarly useful vectors known in the art or otherwise contemplated.

A further embodiment of the presently disclosed and claimed inventive concept(s) is a host cell, made recombinant with a recombinant vector as described herein above. The recombinant host cell may be a prokaryotic cell or a eukaryotic cell. As used herein, the term "engineered" or "recombinant" cell is intended to refer to a cell into which a recombinant gene, such as a gene encoding TS, has been introduced. Engineered cells are thus cells having a gene or genes introduced through the hand of man. Recombinantly introduced genes will either be in the form of a cDNA gene, one or more copies of a genomic gene, or will include genes positioned adjacent to a promoter not naturally associated with the particular introduced gene. In certain embodiments, the recombinant host cell may produce testosteronan.

Where one desires to use a host other than *Comomonas*, as may be used to produce recombinant testosteronan synthase, it may be advantageous to employ a prokaryotic system such as *E. coli*, *B. subtilis*, *Lactococcus* sp., or even eukaryotic systems such as yeast or Chinese hamster ovary, African green monkey kidney cells, VERO cells, or the like. For example but not by way of limitation, the host cell may be selected from the group consisting of a *Bacillus* host such as *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus lichemformis*, *Bacillus megaterium*, *Bacillus stearothermophilus*, *Bacillus subtilis*, *Bacillus thuringiensis*; a *Streptomyces* host such as *Streptomyces lividans* or *Streptomyces murinus*; a gram negative bacteria such as *E. coli* or *Pseudomonas*; a fungus or yeast host such as *Candida*, *Kluyveromyces*, *Pichia*, *Saccharomyces*, *Schizosaccharomyces*, *Yarrowia*, *Acremonium*, *Aspergillus*, *Aureobasidium*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma*. The host cell may also be selected from the group consisting of *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, *Aspergillus aculeatus*, *Aspergillus awamori*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, and *Trichoderma viride*. Of course, where this is undertaken it will generally be desirable to bring the testosteronan synthase gene under the control of sequences which are functional in the selected alternative host. The appropriate DNA control sequences, as well as their construction and use, are generally well known in the art as discussed in more detail herein below.

In certain embodiments, the testosteronan synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which TS DNA sequences are ligated. In particular instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

Nucleotide sequences having testosteronan synthase activity may be isolated by any methods described herein or otherwise contemplated by those of ordinary skill in the art. For example but not by way of limitation, polymerase chain reaction or RT-PCR produced DNA fragments may be obtained which contain full complements of genes or cDNAs from a number of sources, including other strains of *Comomonas* or from other prokaryotic or eukaryotic sources, such as cDNA libraries. Virtually any molecular cloning approach may be employed for the generation of DNA fragments in accordance with the presently disclosed and claimed inventive concept(s). Thus, the only limitation generally on the particular method employed for DNA isolation is that the isolated nucleotide sequences should encode a biologically functional equivalent TS, and in certain embodiments, the isolated nucleotide sequences should encode an amino acid sequence that contains at least one of the TS amino acid motifs described in detail hereinafter.

Once the DNA has been isolated, it is ligated together with a selected vector. Virtually any cloning vector can be employed to realize advantages in accordance with the presently disclosed and claimed inventive concept(s). Typical useful vectors include plasmids and phages for use in prokaryotic organisms and even viral vectors for use in eukaryotic organisms. Generally Regarded As Safe (GRAS) organisms are advantageous in that one can augment the strain's ability to synthesize testosteronan through gene dosaging (i.e., providing extra copies of the testosteronan synthase gene by amplification) and/or the inclusion of additional genes to increase the availability of the testosteronan precursors UDP-GlcUA and UDP-GlcNAc and/or the inclusion of genes that include enzymes that will make modifications (such as sulfation and epimerization) to the testosteronan polymer. For example, the vector may include (or a separate vector may also be inserted into the recombinant host cell that includes) a nucleic acid segments having a coding region encoding UDP-N-acetylglucosamine pyrophosphorylase and/or an enzymatically active UDP-GlcUA biosynthetic pathway enzyme such as UDP-glucose dehydrogenase and UDP-glucose pyrophosphorylase. The inherent ability of a *bacterium* to synthesize testosteronan is also augmented through the formation of extra copies, or amplification, of the plasmid that carries the testosteronan synthase gene. This amplification can account for up to a 10-fold increase in plasmid copy number and, therefore, the TS gene copy number.

Another procedure that would further augment TS gene copy number is the insertion of multiple copies of the gene into the plasmid. Another technique would include integrating the TS gene into chromosomal DNA. This extra amplification would be especially feasible, since the TS gene size is small. In some scenarios, the chromosomal DNA-ligated vector is employed to transfect the host that is selected for clonal screening purposes such as *E. coli* or *Bacillus*, through the use of a vector that is capable of expressing the inserted DNA in the chosen host. In certain instances, especially to confer stability, genes such as the TS gene may be integrated into the chromosome in various positions in an operative fashion. Unlike plasmids, integrated genes do not need selection pressure for maintenance of the recombinant gene.

As described hereinabove, it will also be understood that this presently disclosed and claimed inventive concept(s) is not limited to the particular amino acid and nucleic acid sequences of SEQ ID NOS:1 and 2, respectively. Recombinant vectors and isolated DNA segments may therefore variously include the TS coding regions themselves, coding regions bearing selected alterations or modifications in the basic coding region, or they may encode larger polypeptides which nevertheless include TS coding regions or may encode biologically functional equivalent proteins or peptides which have variant amino acid sequences.

In certain embodiments, any amino acid changes compared to SEQ ID NO:1 include amino acid changes that are of a minor nature; particular non-limiting examples include conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

The DNA segments of the presently disclosed and claimed inventive concept(s) encompass biologically functional equivalent TS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of any techniques known to a person having ordinary skill in the art or otherwise encompassed herein, including but not limited to, site-directed mutagenesis techniques, e.g., to introduce improvements to the enzyme activity or to antigenicity of the TS protein or to test TS mutants in order to examine HS activity at the molecular level.

Also, specific changes to the TS coding sequence may result in the production of testosteronan having a modified size distribution or structural configuration. One of ordinary skill in the art would appreciate that the TS coding sequence can be manipulated in a manner to produce an altered TS, which in turn is capable of producing testosteronan having differing polymer sizes and/or functional capabilities. For example, the TS coding sequence may be altered in such a manner that the TS has an altered sugar substrate specificity so that the TS creates a new testosteronan-like chimeric polymer incorporating a different structure via the inclusion of a previously unincorporated sugar or sugar derivative. This newly incorporated sugar results in a modified testosteronan having different and unique functional properties. Such mutant GAG synthase proteins have been created in other cases including: (a) a single point mutation that changes the size distribution of the vertebate HA synthase (Pummill & DeAngelis, J. B. C., 2003) and (b) the chimeric PmHS1/PmHS2 heparosan synthases that utilize a wider variety of UDP-sugar analogs than either natural sequence heparosan synthase (Otto et al, J. B. C. 2012). As will be appreciated by one of ordinary skill in the art given the TS coding sequence, changes and/or substitutions can be made to the TS coding sequence such that these desired properties and/or size modifications can be accomplished.

Basic knowledge on the substrate binding sites (e.g., the UDP-GlcUA site or UDP-GlcNAc site at the DXD motifs, where D=Glu and X=any amino acid); or the oligosaccharide acceptor site of CtTS allows the targeting of residues for mutation to change the catalytic properties of the site. The identities of important catalytic residues of pmHAS, another GAG synthase, have recently been elucidated (Jing & DeAngelis, 2000, the contents of which are expressly incorporated herein in their entirety). Appropriate changes at or near these residues alters UDP-sugar binding. Changes of residues in close proximity should allow other precursors to bind instead of the authentic testosteronan sugar precursors; thus a new, modified polymer is synthesized. Polymer size changes are caused by differences in the synthase's catalytic efficiency or changes in the acceptor site affinity. Polymer size changes have been made in seHAS and spHAS (U.S. patent application Ser. Nos. 09/559,793 and 09/469,200, the contents of which are expressly incorporated herein by reference) as well as the vertebrate HAS, xIHAS1 (DG42) (Pummill & DeAngelis, 2003, the contents of which are expressly incorporated herein in their entirety) by mutating various residues. Therefore, the presently disclosed and claimed inventive concept(s) encompasses similar or superior versions of mutant CtTS which synthesize modified polymers as well as different sized polymers.

The term "modified structure" as used herein denotes a testosteronan polymer containing a sugar or derivative not normally found in the naturally occurring testosteronan polypeptide. The term "modified size distribution" refers to the synthesis of testosteronan molecules of a size distribution not normally found with the native enzyme; the engineered size could be much smaller or larger than normal.

One of ordinary skill in the art given this disclosure would appreciate that there are several ways in which the size distribution of the testosteronan polymer made by the TS could be regulated to give different sizes. First, the kinetic control of product size can be altered by environmental factors such as decreasing temperature, decreasing time of enzyme action and/or by decreasing the concentration of one or both sugar nucleotide substrates. Decreasing any or all of these variables will give lower amounts and smaller sizes of testosteronan product. The disadvantages of these extrinsic approaches are that the yield of product is also decreased, and it is difficult to achieve reproducibility from day to day or batch to batch. Secondly, the intrinsic ability of the enzyme may be altered to synthesize a large or small testosteronan product. Changes to the protein are engineered by recombinant DNA technology, including substitution, deletion and/or addition of specific amino acids (or even the introduction of prosthetic groups through metabolic processing). Such changes may result in an intrinsically slower enzyme that allows for more reproducible control of testosteronan size by kinetic means. The final testosteronan size distribution is determined by certain characteristics of the enzyme that rely on particular amino acids in the sequence. Among the residues absolutely conserved between the now known GAG synthase enzymes, there is a set of amino acids at unique positions that control or greatly influence the size of the polymer that the enzyme can make.

Structurally modified testosteronan is no different conceptually than altering the size distribution of the testosteronan product by changing particular amino acids in the desired TS. Derivatives of UDP-GlcNAc, in which the acetyl group is missing from the amide (UDP-GlcN) or replaced with another chemically useful group (for example, phenyl to produce UDP-GlcNPhe), is expected to be particularly useful. The free amino group would be available for chemical reactions to derivatize testosteronan in the former case with GlcN incorporation. In the latter case, GlcNPhe would make the polymer more hydrophobic or prone to making emulsions. The strong substrate specificity may rely on a particular subset of amino acids among the residues that are conserved. Specific changes to one or more of these residues create a functional TS that interacts less specifically with one or more of the substrates than the native enzyme. This altered enzyme then utilizes alternate natural or special sugar nucleotides to incorporate sugar derivatives designed to allow different chemistries to be employed for the following purposes: (I) covalently coupling specific drugs, proteins, or toxins to the structurally modified testosteronan for general or targeted drug delivery, radiological procedures, etc. (ii) covalently cross linking the testosteronan itself or to other supports to achieve a gel, or other three dimensional biomaterial with stronger physical properties, and (iii) covalently linking testosteronan to a surface to create a biocompatible film or monolayer.

Another embodiment of the presently disclosed and claimed inventive concept(s) is directed to an isolated, enzymatically active testosteronan synthase encoded by any of the nucleotide sequences described herein above and comprising any of the amino acid sequences described herein above. The testosteronan synthase is a single protein that is a dual-action catalyst that utilizes UDP-GlcUA and UDP-GlcNAc to synthesize a polymer having the repeat structure [-4-D-GlcUA-α1,4-D-GlcNAc-α1-]$_n$. In certain embodiments, the testosteronan synthase is produced recombinantly.

Figure 5:
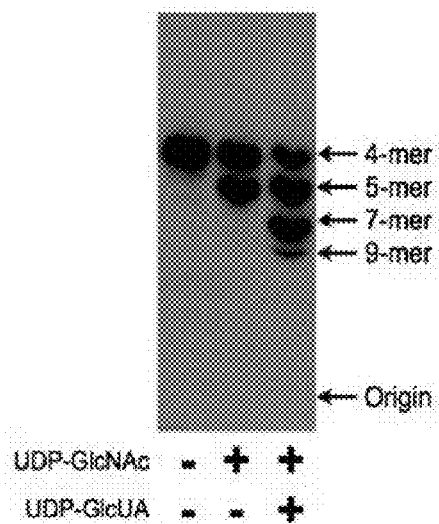
FIG. 5 depicts extension of an $^{125}$I-labeled heparosan tetramer acceptor by CtTS: A radiolabeled heparosan tetrasaccharide was extended in a reaction containing the recombinant *Comamonas testosteronan* synthase lysate, 5 mM MgCl$_2$ and +/− the donor sugars UDP-GlcNAc and UDP-GlcUA. Heparosan tetrasaccharide was prepared as described in (Sismey-Ragatz et al., 2007), but subjected to reductive amination as in (Jing et al., 2006). The Hep$_4$ amine was reacted with Bolton-Hunter reagent (NEN Perkin Elmer, Waltham, Mass.) and purified by butanol extraction. The aqueous phase was used as the acceptor. The reactions were incubated at 30° C. for 3 hours, and stopped with heat inactivation. The reactions were run on high-performance silica thin layer chromatography plates (n-butanol/acetic acid/water, 2.5:1:1) and autoradiographed overnight at −80° C. with an enhancing screen. Heparosan acceptor was elongated by the *Comamonas* synthase.

The presently disclosed and claimed inventive concept(s) is also directed to a method of producing a polymer, at least a portion of which has the repeat structure [-4-D-GlcUA-α1,4-D-GlcNAc-α1-]$_n$. In the method, any of the recombinant, enzymatically active testosteronan synthases described herein above is combined with at least one UDP-sugar (e.g., UDP-GlcUA and/or UDP-GlcNAc) and a functional acceptor that comprises at least one sugar unit. The testosteronan synthase elongates the functional acceptor to provide a polymer having a structure of at least one of [-4-D-GlcUA-α1,4-D-GlcNAc-α1-]$_n$, GlcUA-α1,4-R and D-GlcNAc-α1-4-R—, wherein R comprises any chemical group. In addition, a heparosan polymer with the general repeat structure of [-4-D-GlcUA-α1,4-D-GlcNAc-α1-]$_n$ will also serve as acceptor for CtTS (as shown in FIG. 5 and described in greater detail herein below). Thus, it is possible to create hybrid or chimeric molecules with both types of glycosidic linkages found in heparosan/heparan sulfate/heparin and in testosteronan in a single polymer molecule. Combining the structures found in both the natural human polymers and the novel polymer will allow new avenues of therapeutic design. For example, regions with altered heparin-binding protein or heparin-modifying enzyme interactions (either stronger or weaker depending on the specific polypeptide) may be embedded in the GAG chain to alter its biologic and therapeutic effects.

In certain additional embodiments, the at least one UDP-sugar may be provided in a stoichiometric ratio to the at least one functional acceptor such that the recombinant testosteronan synthase elongates the at least one functional acceptor to provide a polysaccharide having a desired size distribution. The resulting polysaccharide may be substantially monodisperse in size and have a polydispersity value in a range of from 1.0 to 1.5. The desired size distribution is obtained by controlling the stoichiometric ratio of UDP-sugar to functional acceptor.

The term "substantially monodisperse in size" as used herein will be understood to refer to defined glycosaminoglycan polymers that have a very narrow size distribution. For example, substantially monodisperse glycosaminoglycan polymers having a molecular weight in a range of from about 3.5 kDa to about 0.5 MDa will have a polydispersity value (i.e., Mw/Mn, where Mw is the average molecular weight and Mn is the number average molecular weight) in a range of from about 1.0 to about 1.1, and preferably in a range from about 1.0 to about 1.05. In yet another example, substantially monodisperse glycosaminoglycan polymers having a molecular weight in a range of from about 0.5 MDa to about 4.5 MDa will have a polydispersity value in a range of from about 1.0 to about 1.5, and preferably in a range from about 1.0 to about 1.2.

The functional acceptor may comprise at least one sugar unit, such as but not limited to, uronic acid and/or a uronic acid analog comprising a substitution at at least one of the C2 and C3 positions thereof. In certain embodiments, the functional acceptor may comprise at least two sugar units, at least one of which is selected from the group consisting of uronic acid (such as but not limited to, GlcUA, iduronic acid (IdoUA) and GalUA), a uronic acid analog comprising a substitution at at least one of the C2 and C3 positions thereof (such as but not limited to, GlcNAcUA, GlcdiNAcUA, and 2-deoxy-2-fluoro-GlcUA), a hexosamine (such as but not limited to, GlcNAc, GalNAc, GlcN and GalN) and a hexosamine analog comprising a substitution at at least one of the C2 and C6 positions thereof (such as but not limited to, GlcN, GlcNAcNAc, GlcN[TFA], GlcNBut, GlcNPro, and 6-F-6-deoxyGlcNAc). Non-limiting examples of functional acceptors that may be utilized in accordance with the presently disclosed and claimed inventive concept(s) include a testosteronan oligosaccharide, polysaccharide and/or polymer and a heparosan oligosaccharide, polysaccharide and/or polymer.

In one embodiment, the functional acceptor may be a testosteronan oligosaccharide of about 3 sugar units to about 4 kDa, or a testosteronan polymer having a mass of about 4 kDa to about 1 MDa. In another embodiment, the functional acceptor may be a heparosan oligosaccharide of about 3 sugar units to about 4 kDa, or a heparosan polymer having a mass of about 4 kDa to about 2 MDa. In another embodiment, the functional acceptor may be a testosteronan oligosaccharide, polysaccharide or polymer; a heparosan oligosaccharide, polysaccharide or polymer; a heparin oligosaccharide, polysaccharide, or polymer; a heparin oligosaccharide, polysaccharide or polymer; a heparosan-like oligosaccharide, polysaccharide or polymer; or a sulfated or modified oligosaccharide, polysaccharide or polymer, or a GlcUA-based or GlcUA-analog glycoside. In yet another embodiment, the functional acceptor may be an extended acceptor such as testosteronan chains, heparosan chains, mixed glycosaminoglycan chains, analog containing chains or any combination thereof.

Figure 20:
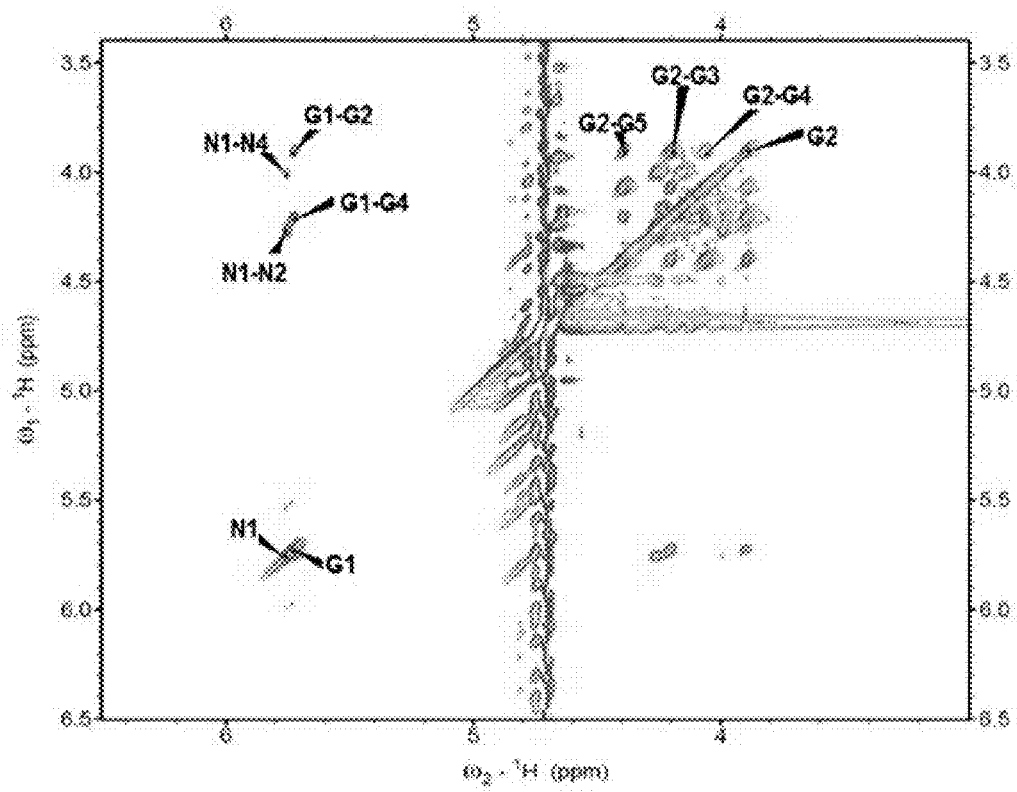
FIG. 20 contains two-dimensional $^1$H-$^1$H total correlation spectrum (TOCSY) of the synthetic *Comomonas* polysaccharide at 338K. The spectrum was recorded at 800 MHz on a Bruker Avance II spectrometer. Mixing time 120 ms; delay time 1.5 seconds; acquisition time 0.852 s.

Another functional acceptor class that may be utilized in accordance with the presently disclosed and claimed inventive concept(s) includes synthetic glycosides (i.e., sugars that have a non-sugar component at the reducing end) or similar synthetic carbohydrates. These molecules are less expensive and can possess useful groups. Glucuronic acid and its glycosides, after two step-wise extensions prior to reaction synchronization, are effective acceptors with CtTS (as seen in FIG. 20 and described in further detail herein below).

The functional acceptor may further include a moiety selected from the group consisting of a fluorescent tag, a radioactive tag or therapeutic, an affinity tag, a detection probe, a medicant, a biologically active agent, a therapeutic agent, and combinations thereof. As a non-limiting example, an artificial para-nitrophenyl moiety was used in the acceptor glycoside; thus, the resulting testosteronan chains have an attached non-sugar group. In addition, the UDP-sugar and/or UDP-sugar analog may be radioactive or nuclear magnetic resonance-active.

The method may further include the step of providing a divalent metal ion, such as but not limited to, manganese, magnesium, cobalt, nickel and combinations thereof. In addition, the method may be carried out in a buffer having a pH from about 4 to about 9.

A yet further embodiment of the presently disclosed and claimed inventive concept(s) is directed to an additional method of producing a polymer, wherein at least a portion of which has the repeat structure [-4-D-GlcUA-α1,4-D-GlcNAc-α1-]$_n$. In the method, any of the recombinant host cells described herein above is cultured under conditions that allow for the production of a polymer having the repeat structure [-4-D-GlcUA-α1,4-D-GlcNAc-α1-]$_n$. The resultant polymer may further be isolated and/or purified, either from the culture medium or the recombinant host cell. The recombinant host cell may include (either genomically or through the addition of a vector) nucleic acid segments encoding enzymes which produce UDP-GlcUA and UDP-GlcNAc. If the recombinant host cell does not produce the sugar precursors, UDP-GlcUA and UDP-GlcNAc may be supplied to the recombinant host cell.

Another embodiment of the presently disclosed and claimed inventive concept(s) is directed to another method of producing the testosteronan polymers described herein. In this method, native host cells are cultured under conditions that allow for the production of a polymer having the repeat structure [-4-D-GlcUA-α1,4-D-GlcNAc-α1-]$_n$; the polymer so produced is then isolated from the native host cells. Non-limiting examples of native host cells that may be utilized in accordance with the presently disclosed and claimed inventive concept(s) include *Comomonas* species, such as but not limited to, *Comomonas testosteroni*, or *Pseudomonas allies*, or any other microbe that possessing a functional testosteronan synthase or homolog or analog. The polymer so produced may further be purified by any methods described herein or otherwise known in the art.

The presently disclosed and claimed inventive concept(s) further includes isolated and/or purified testosteronan polymers (as well as testosteronan-like (testosteronan-based) polymers) produced by any of the methods described herein above. In certain embodiments, the isolated/purified testosteronan polymers may be recombinantly produced and/or substantially monodisperse in size (as described in detail herein above). The isolated/purified testosteronan polymers produced in accordance with the presently disclosed and claimed inventive concept(s) may be substantially insensitive to digestion by a degrading enzyme that acts upon at least one of heparosan, heparin, heparan sulfate, chondroitin and hyaluronan. The isolated/purified testosteronan polymers may also be sulfated.

EXAMPLES

Examples are provided herein below. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

Figure 2:
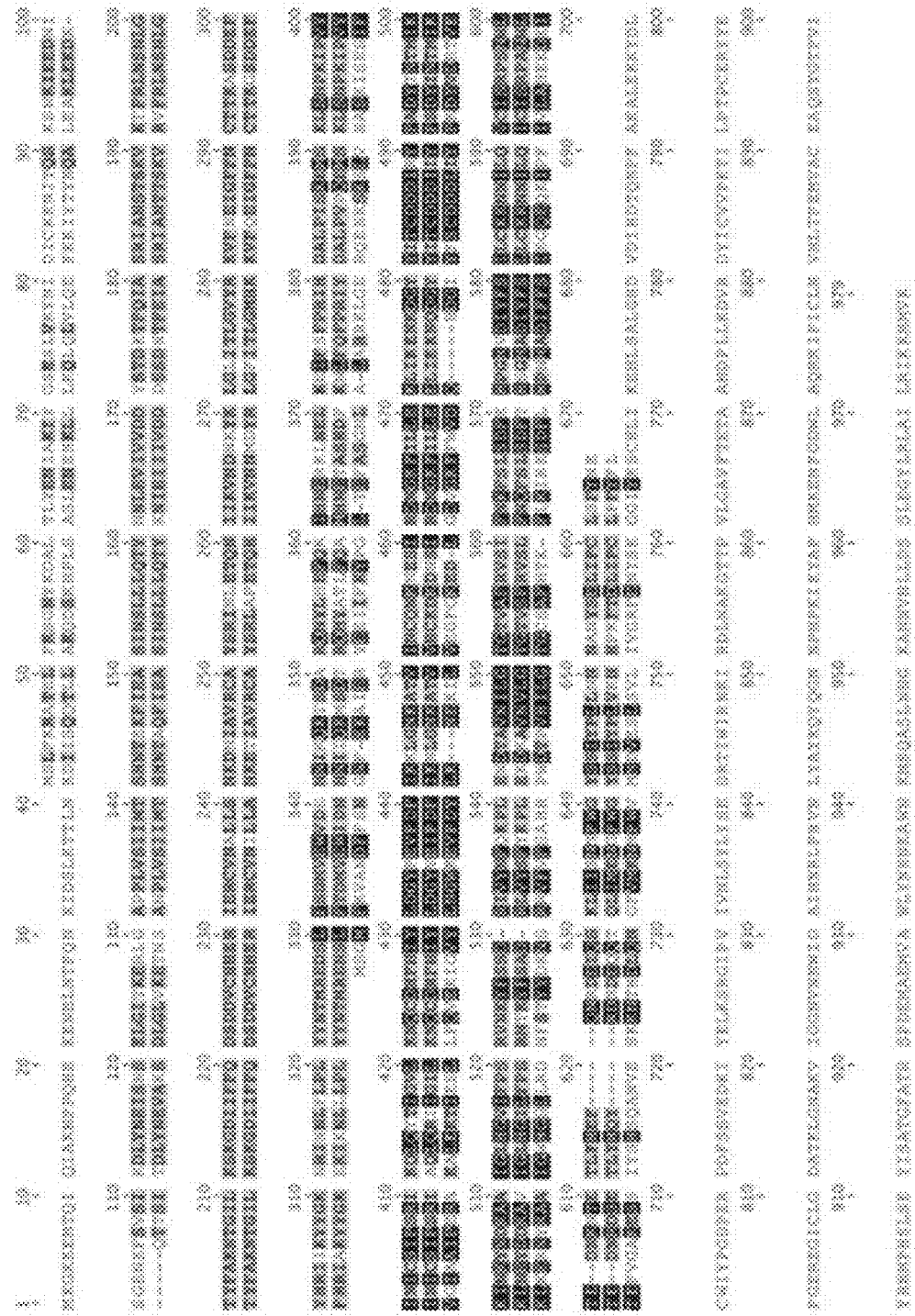
FIG. 2 depicts a sequence alignment of the *Pasteurella* glycosaminoglycan synthases PmHS1 (top; SEQ ID NO:5) and PmHS2 (middle; SEQ ID NO:6) with the *Comamonas testosteronan* synthase CtTS (bottom; SEQ ID NO:1). The PmHS GT45 domains are 32% identical to that of the *Comamonas testosteronan* synthase (Global alignment with Blosum62 cost matrix and free end gaps. Geneious 4.7.6. Auckland, New Zealand) (Drummond et al., 2010).

Example 1: *Comomonas* Testosteronansynthase, a Bifunctional Glycosyltransferase That Produces a Unique Heparosan Polysaccharide Analog Recently, the distinct catalytic phenotypes exhibited by the two *Pasteurella multocida* heparosan synthases were reported (Sismey-Ragatz et al., 2007). As a part of the efforts to better understand the mechanism of these GAG synthases, including the structure/function relationship that manifests donor and acceptor specificity, a search of the NCBI sequence databases identified a potential bifunctional glycosyltransferase [GT] (ZP_03542636; 32% identity, FIG. 2) in the genome of the *Comamonas testosteroni* KF-1 isolate with a region of sequence similarity to the CAZy GT45 family of glycosyltransferases (Cantarel et al., 2009). The CAZy GT45 family of proteins contains only eight members; as of January 2011, the CAZy glycosyltransferase database contained 92 families with approximately 65,000 GT modules. The bifunctional *P. multocida* heparosan synthases contain this relatively rare GT45 domain that, in combination with a GT2 domain, synthesizes the GAG heparosan that comprises the capsule of type D *P. multocida*. Another similar pair of proteins, the single action glycosyltransferases KfiA and KfiC of *E. coli* K5, together also make heparosan; the former is a GT45-containing enzyme. In the studied GT45 enzymes, the activity is a retaining glycosyltransferase. For PmHS1, PmHS2 and KfiA, an α1,4-linked D-GlcNAc is formed; thus, these catalysts have utility for generating a linkage found in heparosan, the precursor polysaccharide to heparan sulfate and heparin.

In this Example, it is demonstrated that the ZP_03542636 gene is responsible, in part, for forming a GAG-like polysaccharide in *Comamonas testosteroni* KF-1. The *Comamonas testosteroni* KF-1 gene product is a novel bifunctional GAG synthase (possessing an N-terminal GT45 domain and a new prototype GT family domain GT93 at the C-terminus) that is referred to herein as "CtTS". The polysaccharide backbone produced by CtTS is a previously unidentified GAG, referred to herein as "testosteronan", possessing the structure [-4-D-GlcUA-α1,4-D-GlcNAc-α1-]$_n$.

Results of Example 1

Figure 3:
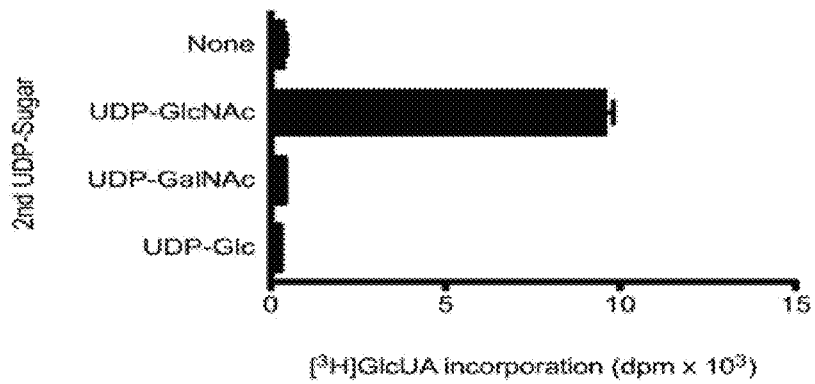
FIG. 3 graphically depicts the donor specificity of CtTS. Activity assays were performed using recombinant *Comamonas testosteronan* synthase with either radiolabeled UDP-[$^3$H]GlcUA (left panel) or UDP-[$^3$H]GlcNAc (right panel) and the indicated unlabeled UDP-sugar or no precursor (None). Vector only lysates in the presence of UDP-[$^3$H]GlcUA or UDP-[$^3$H]GlcNAc gave values of ~200 dpm. These activity assays reveal a preference for UDP-GlcNAc as the hexosamine sugar, and UDP-GlcUA as the uronic acid sugar, the identical precursors employed by both heparosan and hyaluronan synthases.
Figure 3:
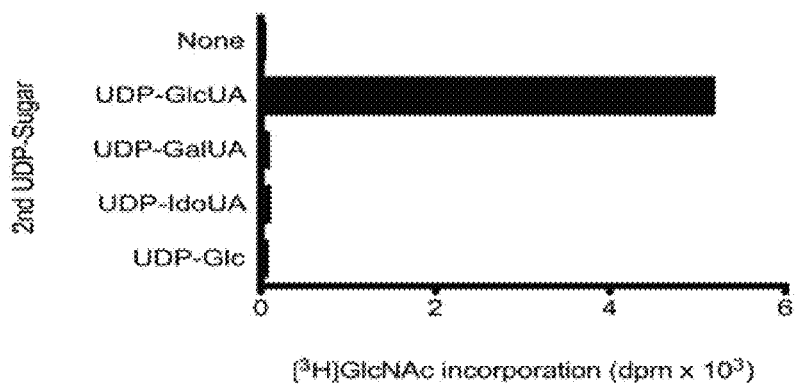

Donor Sugar Specificity of CtTS: By sequence comparison with the *Pasteurella* heparosan synthases, CtTS is predicted to possess α-GlcNAc-transferase activity due to the presence of a GT45 family domain. However, both PmHAS and PmCS also exhibit high sequence identity, yet they transfer distinct monosaccharides from the donor molecules UDP-GlcNAc and UDP-GalNAc, respectively (Jing et al., 2000). In order to determine the preferred hexosamine sugar donor utilized for putative GAG-like heteropolysaccharide biosynthesis, activity assays were performed with clarified lysates from recombinant bacteria expressing CtTS using two different UDP-sugars simultaneously in polymerization reactions in vitro. Specifically, radiolabeled UDP-[$^3$H]GlcUA was employed as a traceable precursor and either unlabeled UDP-GlcNAc, UDP-GalNAc or UDP-Glc as the second precursor. Significant activity was seen in the presence of UDP-GlcNAc, but not with UDP-GalNAc or UDP-Glc (FIG. 3A); without any UDP-hexosamine, the signal due to incorporation of [$^3$H]GlcUA was the same as vector-alone control lysates. This result was confirmed with the converse polymerization experiment, which was performed with radiolabeled UDP-[$^3$H]GlcNAc and unlabeled UDP-GlcUA. To assess if this uronic acid was the preferred donor, radiochemical incorporation assays were also performed with UDP-[$^3$H]GlcNAc in the presence of either UDP-GlcUA, UDP-GalUA, UDP-IdoUA (Weïwer et al., 2008) or UDP-Glc as the second precursor; only the reactions containing UDP-GlcUA showed significant incorporation (FIG. 3B). Therefore, simultaneous incubation of CtTS with both UDP-GlcUA and UDP-GlcNAc was required for the polymeric signal. In summary, these results demonstrate that CtTS is a bifunctional enzyme capable of forming polysaccharide composed of GlcNAc and GlcUA in vitro. These are the same two sugars found in both hyaluronan and heparosan. By further studying acceptor specificity and using GAG degrading enzymes that are specific for these GAGs, the nature of the polysaccharide formed by CtTS in vitro was characterized.

In this Example, it is demonstrated that this *Comamonas testosteroni* KF-1 gene product is a novel bifunctional GAG synthase (possessing an N-terminal GT45 domain and a new prototype GT family domain GT93 at the C-terminus) that is referred to herein as "CtTS". The polysaccharide backbone produced by CtTS is a previously unidentified GAG, that is referred to herein as "testosteronan", possessing the structure [-4-D-GlcUA-α1,4-D-GlcNAc-α1-]$_n$.

Results of Example 1

Figure 4:
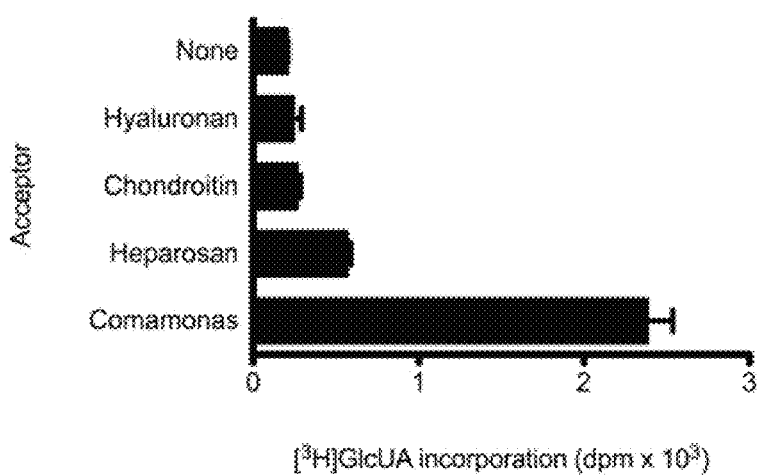
FIG. 4 graphically depicts the acceptor specificity of CtTS. Extension of exogenous polysaccharide by recombinant *Comamonas testosteronan* synthase was measured. Activity assays were performed with radiolabeled UDP-sugars in the presence of hyaluronan, unsulfated chondroitin, heparosan or sonicated *Comamonas* polysaccharide. This result was reproduced with hyaluronan and heparosan tetrasaccharide acceptors; only the heparosan tetrasaccharide gave a substantial signal. The *Comamonas* synthase shows a preference for both heparosan and the *Comamonas* polysaccharide as acceptor molecules.

Acceptor Specificity of CtTS: To identify the acceptor preference of CtTS, radiolabeled sugar polymerization assays were performed in the presence of various GAG acceptors. In many, but not all, GAG synthases, exogenous cognate polysaccharide will increase the signal in sugar incorporation assays by bypassing the slower de novo initiation phase (DeAngelis et al., 1999 and 2004); the elongation phase is much more rapid; thus, higher activity is observed. Typically, non-cognate GAG polymers with different glycosidic linkage patterns are very poor or non-functional acceptors for the known GAG synthases in vitro. Hyaluronan, unsulfated chondroitin and heparosan as well as polysaccharide extract from *C. testosteroni* were tested. Hyaluronan and heparosan tetrasaccharides were also tested for their abilities to act as acceptors. CtTS showed a clear preference for the *Comamonas* polysaccharide, but was also able to use heparosan (FIG. 4). To confirm that CtTS is able to directly extend a heparosan acceptor so as to rule out an artifactual stabilizing or conformational effect in the radio-assays, an $^{125}$I-labeled tetrasaccharide heparosan acceptor was also tested in vitro in the presence of only UDP-GlcNAc for single sugar addition, or UDP-GlcNAc and UDP-GlcUA for polymerization. The *Comamonas testosteroni* synthase was able to extend $^{125}$I-labeled heparosan tetrasaccharide (FIG. 5).

In summary, CtTS is capable of utilizing heparosan and *Comamonas* polysaccharide as acceptors, but not hyaluronan or chondroitin. The failure to extend hyaluronan, which consists of the same sugars as heparosan (which is extended), indicates that the glycosidic linkages are not compatible with a structure required for polysaccharide extension. This could be due to either lack of acceptor binding, or binding in a mode that does not orient the acceptor in an appropriate configuration with respect to the donor sugar for extension. The chondroitin acceptor contains a GalNAc sugar in place of GlcNAc and may also be unable to bind, or binds in a way that it cannot be extended. The finding that heparosan is extended by CtTS in vitro, but not as well as the *Comamonas* extract, suggests that the two polysaccharides share some structural features, but are not identical.

Metal Dependence of CtTS: Many glycosyltransferases require a divalent cation (e.g., $Mg^{2+}$, $Mn^{2+}$, $Ca^{2+}$, etc.) in order to coordinate the UDP-sugar donor molecule for nucleophilic attack by the acceptor molecule. The *Streptococcus* hyaluronan synthase prefers $Mg^{2+}$ while the *Pasteurella* hyaluronan and heparosan synthases prefer $Mn^{2+}$ (DeAngelis, 1996). The difference in metal preference in vitro may be an indication of differences in coordination geometry at the active site structures and/or in the reaction mechanisms.

Using radiolabeled sugar incorporation assays performed in the presence of one or both of these divalent cations, it was observed that the Ct synthase prefers to use $Mg^{2+}$. The presence of 5 mM $Mn^{2+}$ supported GT activity, but activity achieved in the presence of 5 mM $Mg^{2+}$ was roughly twice as for $Mn^{2+}$. Metal is required, as the chelator EDTA eradicated the polymerization signal. Control assays in which lysates were pre-treated with 2 mM EDTA then excess $Mg^{2+}$ was added back supports the conclusion that only the preferred cation $Mg^{2+}$ is required for CtS activity.

Analysis of *C. testosteroni* Polysaccharide: The native target polysaccharide yield from 1-liter culture of *C. testosteroni* in CDM medium after 24 hours was approximately 2 mg. Using complete acid hydrolysis of the purified polysaccharide extract into monosaccharides, followed by anion exchange chromatography, GlcUA and GlcNAc were observed (data not shown); the presence of GlcUA was consistent with the presence of a UDP-glucose 6-dehydrogenase gene adjacent to the CtTS gene in the *C. testosteroni* KF-1 genome. Gel analysis of the cetylpyridinium chloride (CPC) precipitated native polysaccharide and the synthetic polysaccharide made with recombinant CtTS in vitro revealed products with apparent molecular weights of approximately 60 kDa based on HA standards.

Figure 6:
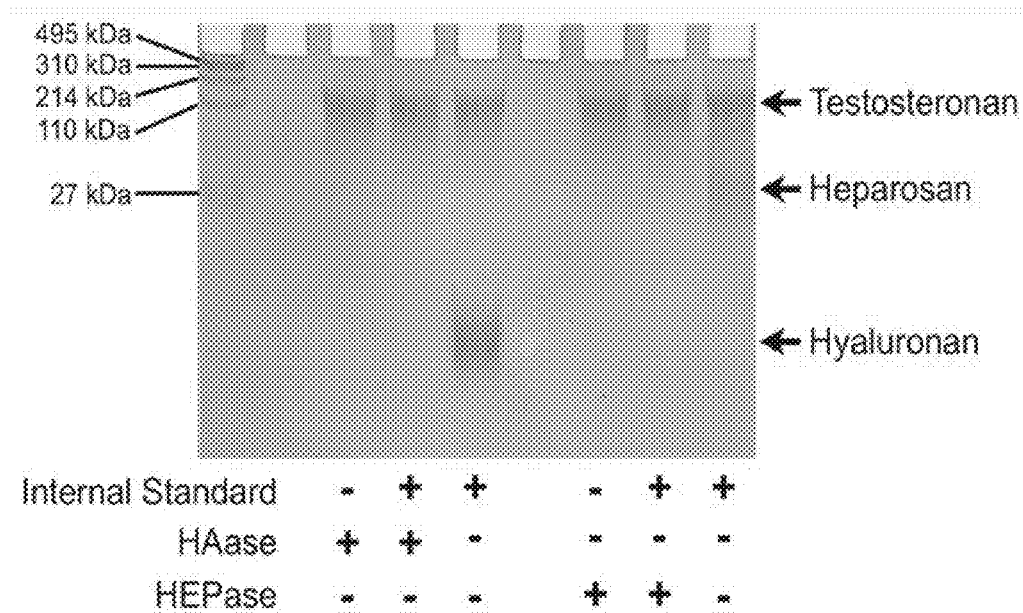
FIG. 6 illustrates a GAG degrading enzyme challenge of synthetic polysaccharide. In vitro synthesized polysaccharide was subjected to heparin lyase III from *Pedobacter heparinus* (HEPase) or ovine testicular hyaluronidase (HAase) digestion; as a control, in parallel reactions sensitive polysaccharides (30 kDa heparosan or 10 kDa hyaluronan, respectively) were co-incubated in the appropriate reaction as internal standards. Reactions were subsequently run on 6% polyacrylamide gel and stained with Alcian Blue dye. The *Comamonas* polysaccharide is insensitive to digestion by both enzymes; similar results were observed for the native polysaccharide. Heparin lyase I and II also did not digest testosteronan (not shown).

The preference for heparosan acceptor over hyaluronan and chondroitin in the radiochemical incorporation assays (FIG. 4), as well as the sequence similarity with PmHS1 and PmHS2, initially suggested that CtTS was akin to heparosan synthase. However, both the native polysaccharide as well as the synthetic polysaccharide were insensitive to degradation by heparin lyase III or ovine testicular hyaluronidase (FIG. 6) as well as *Streptomyces hyalurolyticus* HA lyase, *Proteus vulgaris* chondroitinase ABC, or heparin lyases I or II. The synthetic polysaccharide has no possibility of any potential post-polymerization modifications made by *Comamonas* in vivo that could block the action of the GAG digesting enzymes. Because of this finding, it is believed that while CtTS is able to utilize heparosan as an acceptor molecule due to a hypothetical shared structural feature, this GAG is not the native substrate.

Figure 7:
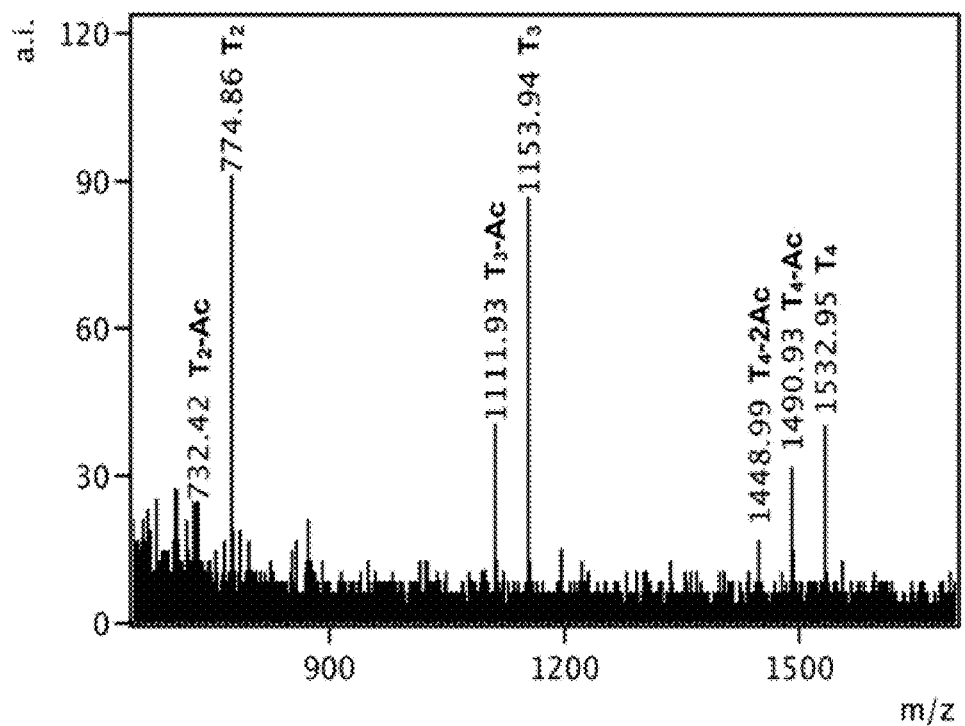
FIG. 7 contains MALDI-TOF mass spectra of acid hydrolyzed *Comamonas* native polysaccharide. Purified *Comamonas* polysaccharide was subjected to partial acid hydrolysis by treatment with 1 M HCl at 95° C. for 15 minutes. The resulting ladder pattern of mass peaks is virtually identical to that seen when acid hydrolysis is performed with either hyaluronan or heparosan or synthetic polysaccharide (not shown). Note the presence of deacetylation peaks (−42 Da) which is also diagnostic of these GAGs. T=[GlcUA-GlcNAc]; Ac=acetyl group.

Due to the inability to digest the *C. testosteroni* polysaccharide with known GAG degrading enzymes, partial acid hydrolysis was employed to produce oligosaccharides that would be suitable for further analysis. Thin layer chromatography (TLC) was used to optimize conditions (not shown) and confirmed the presence of sugar oligomers after hydrolysis. MALDI-ToF mass spectrometry analysis yielded a ladder pattern of mass peaks that is indicative of a backbone with a repeating disaccharide pattern (i.e., 1:1 ratio of N-acetyl-hexosamine to uronic acid) (FIG. 7). Indeed, the fragment mass values were virtually identical to those seen with both heparosan and hyaluronan. The in vitro synthesized polymer mass spectral data was virtually identical to the native polysaccharide; however, it should be noted that such acidic conditions would also potentially remove labile modifications of the backbone. Under these conditions, many N-acetyl groups were removed (as in heparosan or HA). Therefore, in theory, the native polysaccharide could contain derivatives of the more well-known monosaccharide units, but such putative modifications may escape detection after hydrolysis.

These mass spectral data, in combination with the in vitro synthesis of this GAG and the inability to digest both the in vitro and native polysaccharide with various known GAGases, led to the conclusion that this polysaccharide backbone was in fact a new GAG with distinct glycosidic linkages from those of both hyaluronan and heparosan. In keeping with the tradition of naming GAGs based on their initial origin, this new polysaccharide backbone has been termed "testosteronan".

Figure 8:
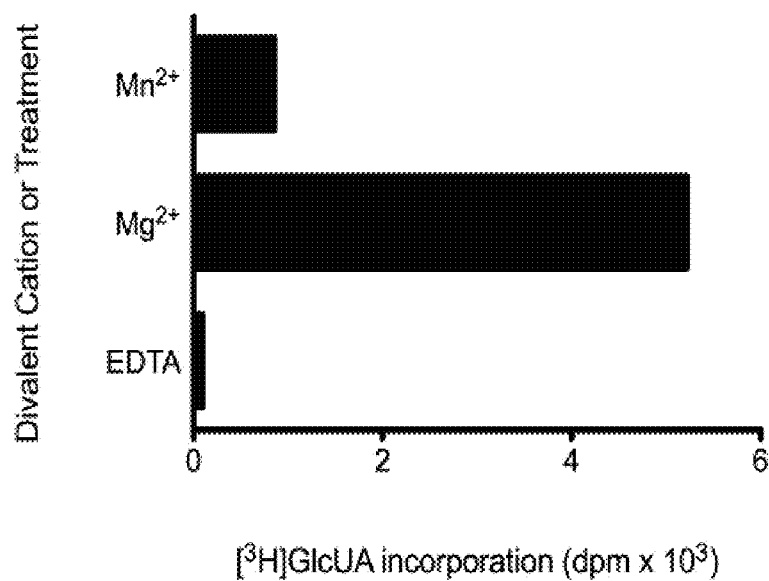
FIG. 8 graphically depicts divalent cation specificity of CtTS: Divalent cation usage by recombinant *Comamonas testosteronan* synthase was measured. Radiolabeled sugar incorporation assays were performed (30 minutes at 22° C., as described in methods) in the presence of 5 mM Mg$^{2+}$ or 5 mM Mn$^{2+}$ or 2 mM EDTA. Lysates containing the recombinant *Comamonas* CtTS gene product show a preference for the divalent cation Mg$^{2+}$.
Figure 9:
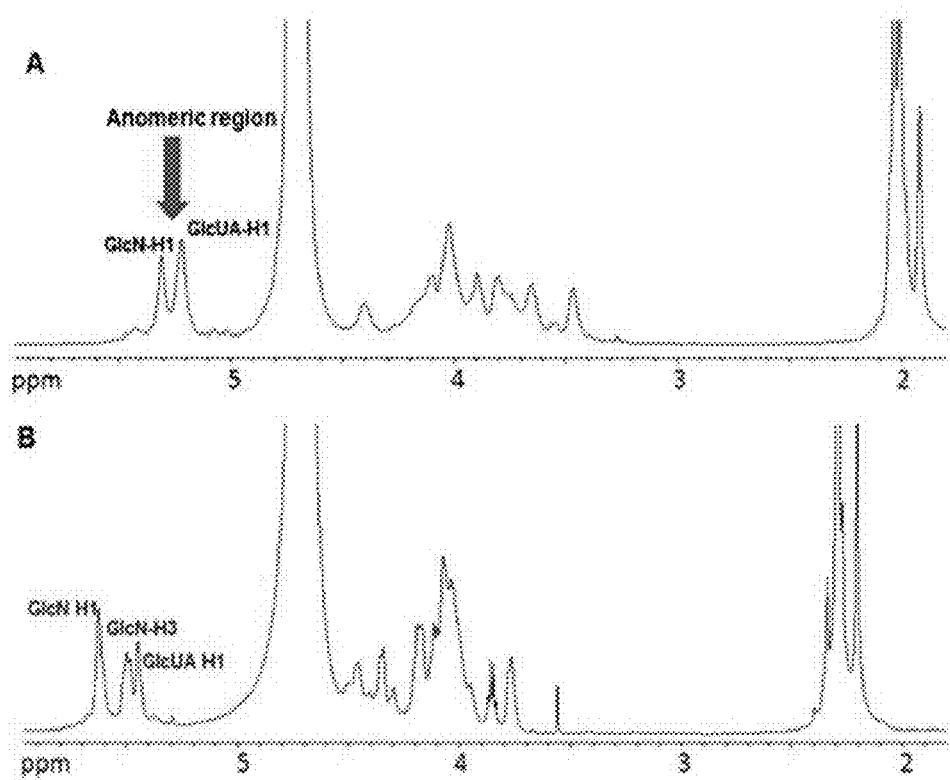
FIG. 9 contains $^1$H-NMR spectra of the native *Comamonas* polysaccharide at 298K (A); 328K (B). The spectrum was recorded at 600 MHz on a Bruker Avance II spectrometer. Sweep width 20.5 ppm; acquisition time 2.65 seconds.
Figure 10:
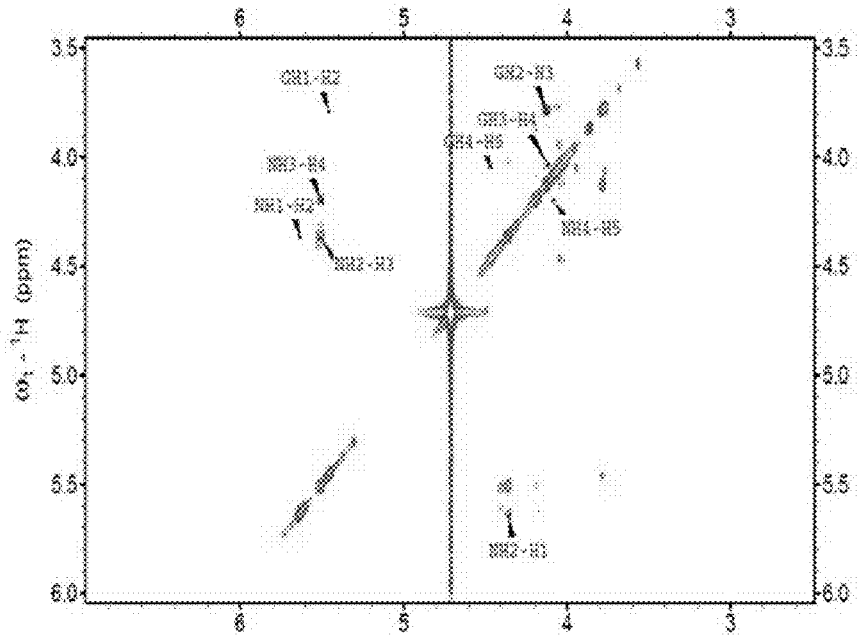
FIG. 10 contains two-dimensional $^1$H-$^1$H correlation spectrum (COSY) of the native *Comamonas* polysaccharide at 328K. The spectrum was recorded at 600 MHz on a Bruker Avance H spectrometer. Sweep width of 12.33 ppm; acquisition time 0.270 s.
Figure 11:
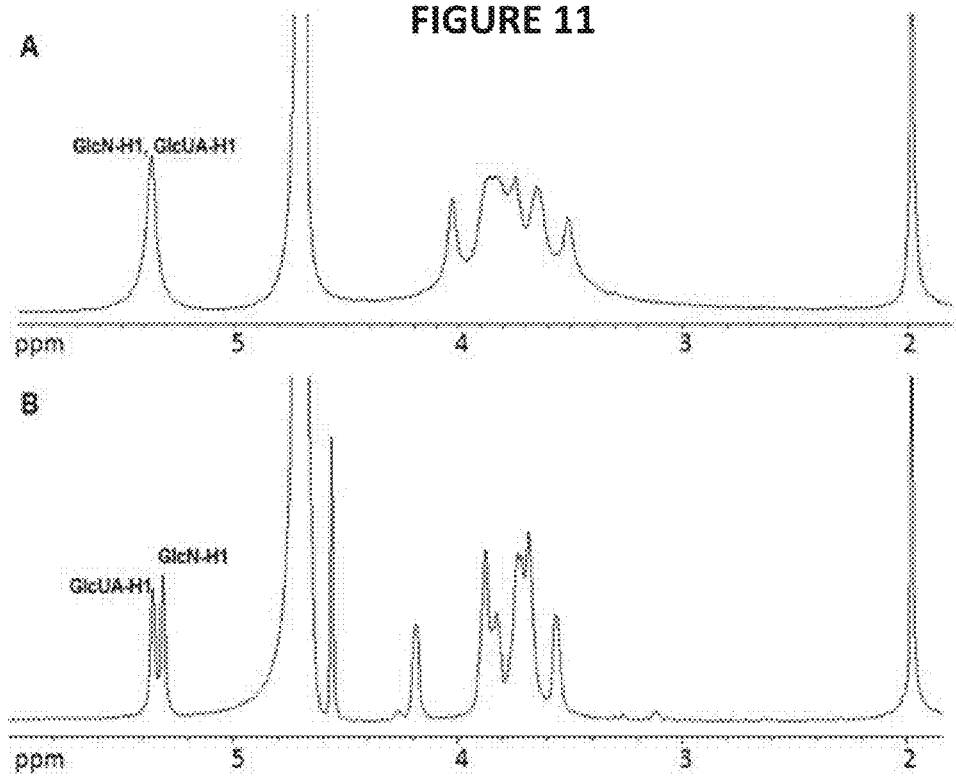
FIG. 11 contains $^1$H-NMR spectra of the synthetic *Comamonas* polysaccharide at different pD (pD is the equivalent of pH in deuterated water solutions). T: 298K, pD 6.9 (A); 298K, pD 3.6 (B). The spectrum was recorded at 600 MHz on a Bruker Avance II spectrometer. Sweep width 20.55 ppm; acquisition time 2.650 s.
Figure 12:
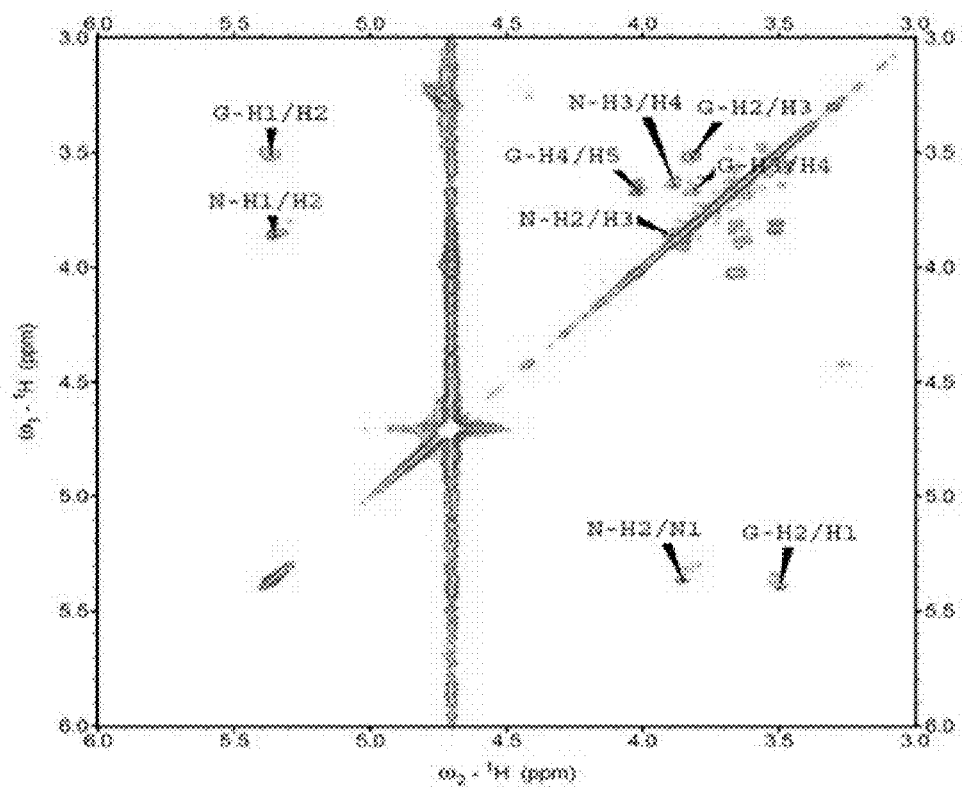
FIG. 12 contains two-dimensional $^1$H-$^1$H correlation spectrum (COSY) of the synthetic *Comamonas* polysaccharide at 298K. The spectrum was recorded at 800 MHz on a Bruker Avance II spectrometer. Sweep width 12.33 ppm; acquisition time 0.270 s.
Figure 13:
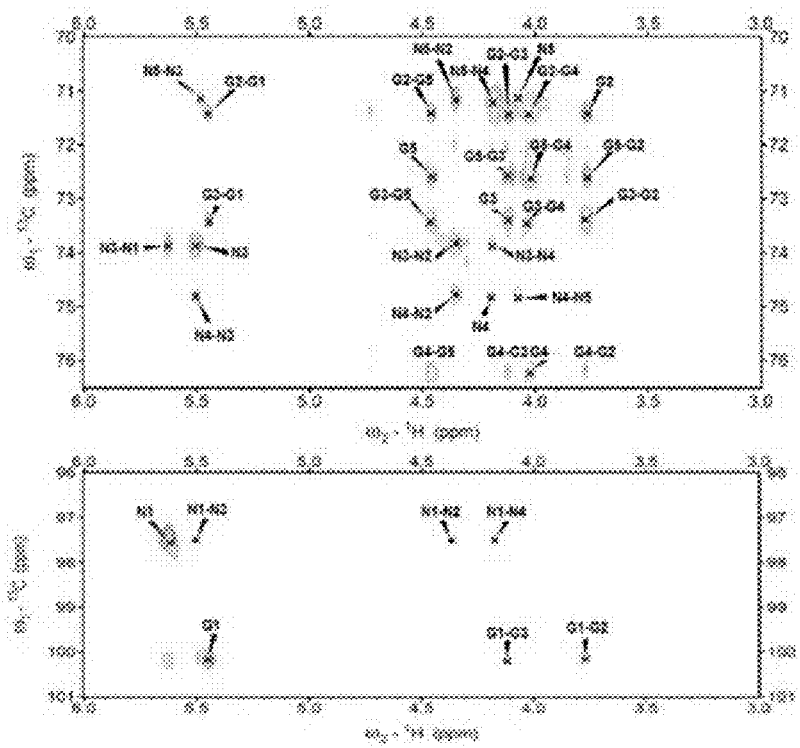
FIG. 13 contains strip plots from 2D ge-HMQC-TOCSY spectrum of the native *Comamonas* polysaccharide at pD 6.9; T 328K: HMQC spectrum (green) was overlaid onto HMQC-TOCSY spectrum (red). The spectrum was recorded at 600 MHz on a Bruker Avance II spectrometer with probe temperature of 328K. Mixing time 50 ms; delay time 1 seconds; acquisition time 0.232 s FIG. 14 contains two-dimensional $^1$H-$^{13}$C correlation spectrum (HMQC) of the native *Comamonas* polysaccharide at 328K. HMQC spectrum (A); the selected region of the spectrum (B). The spectrum was recorded at 800 MHz on a Bruker Avance II spectrometer. Acquisition time 0.330 s.
Figure 14:
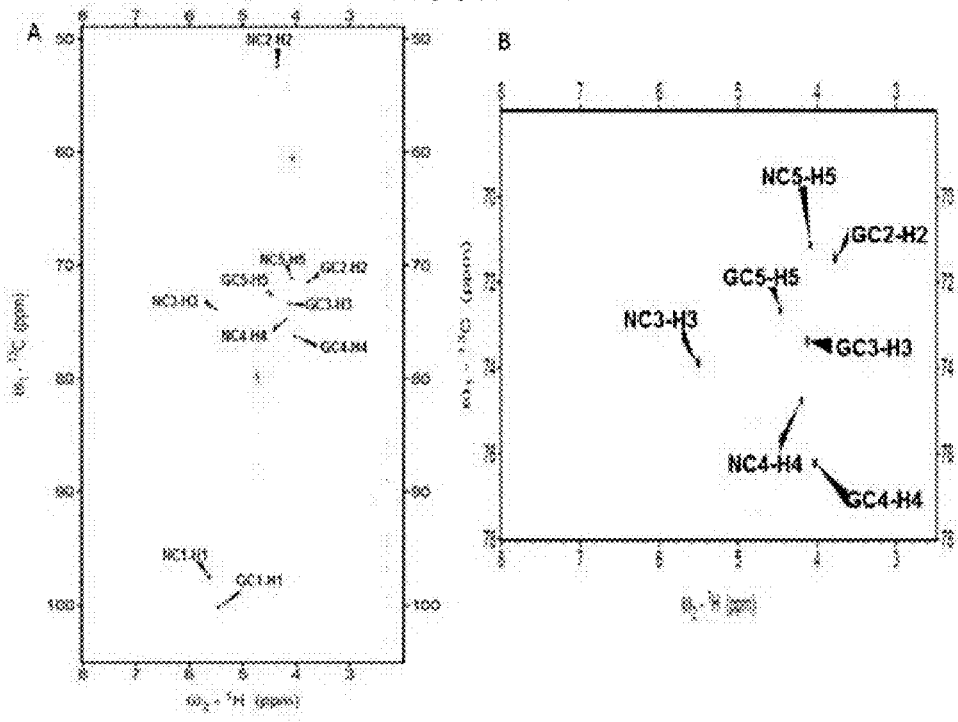
Figure 15:
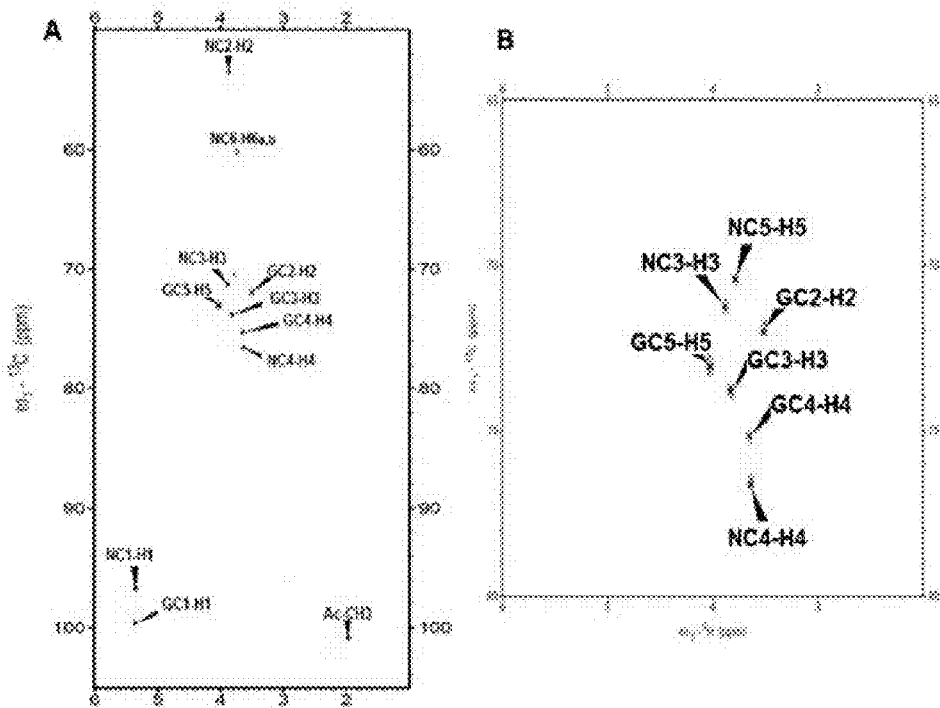
FIG. 15 contains two-dimensional $^1$H-$^{13}$C correlation spectrum (HMQC) of the synthetic *Comamonas* polysaccharide at 298K. HMQC spectrum (A); the selected region of the spectrum (B). The spectrum was recorded at 600 MHz on a Bruker Avance II spectrometer. Acquisition time 0.333 s.
Figure 16:
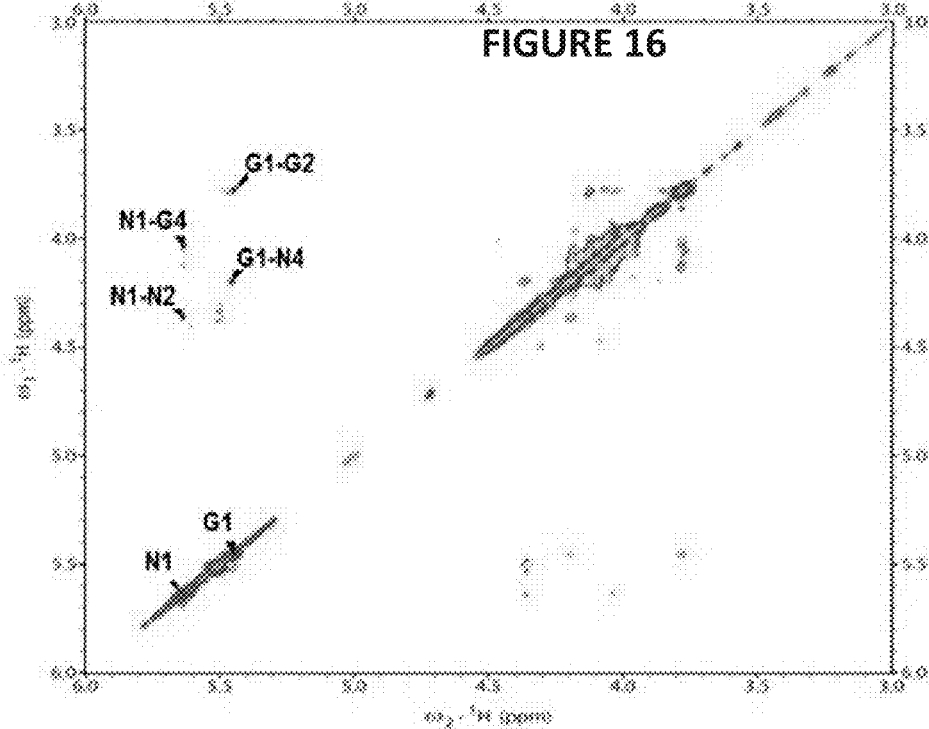
FIG. 16 contains $^1$H-$^1$H NOESY spectrum of the native *Comamonas* polysaccharide at pD 6.9; T 328K. The GlcUA residues are labeled G and the GlcNAc residues are labeled N. The spectrum was recorded at 800 MHz on a Bruker Avance II spectrometer with probe temperature of 328K. Mixing time 400 ms; delay time 1.5 seconds; acquisition time 0.852 s.
Figure 17:
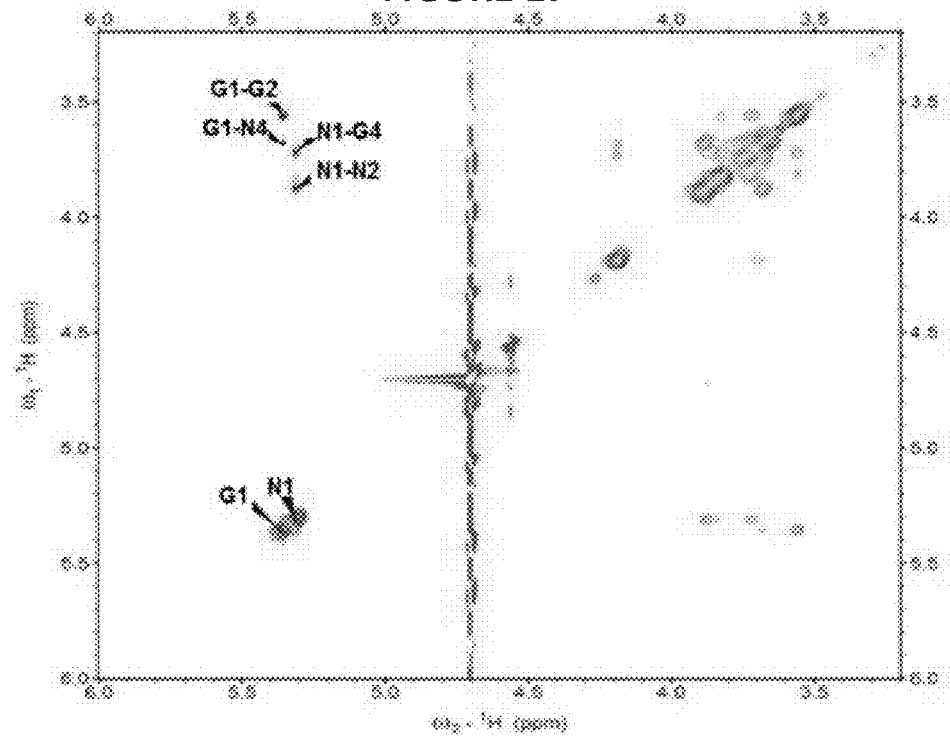
FIG. 17 contains $^1$H-$^1$H NOESY spectrum of the synthetic *Comamonas* polysaccharide at pD 3.6; T 328K: The GlcUA residues are labeled G and the GlcNAc residues are labeled N. The spectrum was recorded at 600 MHz on a Bruker Avance II spectrometer with probe temperature of 328K. Mixing time 400 ms; delay time 1.5 seconds; acquisition time 0.852 s.

NMR determination of a novel glycosaminoglycan: 1D $^1$H and $^{13}$C spectroscopy were initially used to evaluate the structure of both the native and synthetic polysaccharides. These polysaccharides had similar but not identical spectral properties with 14 carbon signals, consistent with a repeating disaccharide unit of GlcUA and GlcNAc. The anomeric signals of each type of monosaccharide residue were assigned based on their characteristic downfield positions (FIG. 8). Next, 2D COSY ($^1$H-$^1$H) and HMQC ($^{13}$C-$^1$H) (FIGS. 9-12) experiments were used to assign all signals to each proton and carbon within the two polysaccharides (Table 2). 2D ge-HMQC-TOCSY (FIG. 13) confirmed all of these assignments. FIG. 13 shows HMQC (Green italics) spectrum of native *Comamonas* polysaccharide overlaid onto ge-HMQC-TOCSY (Red italics) spectrum. 2D TOCSY ($^1$H-$^1$H) (FIGS. 14 and 15) was used to obtain all possible correlations within each spin system. Finally, 2D NOESY (FIGS. 16 and 17) was used to assign NOE signals between the anomeric protons and H-4 protons of the adjacent saccharide residue across the glycosidic linkage to provide linkage positions.

TABLE 2

Chemical shift values (pD 7.0, 25° C.) and assignments of $^1$H and $^{13}$C NMR shifts for *Comamonas testosteroni* polysaccharides.

| Residue/position | Native polysaccharide | | Synthetic polysaccharide | |
| --- | --- | --- | --- | --- |
| | $^{13}$C | $^1$H | $^{13}$C | $^1$H |
| GlcUA 1 | 99.994 | 5.210 | 99.685 | 5.356 |
| GlcUA 2 | 71.306 | 3.465 | 71.995 | 3.508 |
| GlcUA 3 | 73.280 | 3.805 | 73.850 | 3.819 |
| GlcUA 4 | 76.166 | 3.646 | 75.262 | 3.646 |
| GlcUA 5 | 71.723 | 4.025 | 73.130 | 4.020 |
| GlcNAc 1 | 97.409 | 5.301 | 96.722 | 5.349 |
| GlcNAc 2 | 51.957 | 4.109 | 53.470 | 3.861 |
| GlcNAc 3 | 73.432 | 5.222 | 71.275 | 3.868 |
| GlcNAc 4 | 73.869 | 4.008 | 76.536 | 3.625 |
| GlcNAc 5 | 68.398 | 4.001 | 70.472 | 3.771 |
| GlcNAc 6a,b | 61.114 | 3.770 | 60.136 | 3.745 |
| GlcNAc (CH$_3$) | 20.040 | 2.023 | 21.931 | 1.983 |

Based on these spectral data, the structure of the native polysaccharide backbone could be definitively assigned as [-4-D-GlcUA-α1,4-D-GlcNAc-α1-]$_n$; however, the proton at the 3-position of the GlcNAc residue was shifted downfield by 1.354 ppm, compared with the synthetic polysaccharide to 5.222 ppm, suggesting it carried a deshielding modification. One hypothesis is that during biosynthesis of testosteronan, the polysaccharide is polymerized by the CtTS synthase, and then during a post-polymerization step or reaction, the C3 hydroxyl is modified. An alternative model is that a novel hexosamine unit is used by this organism in vivo, but that the enzyme tolerates GlcNAc as observed in the in vitro tests. To date, the nature of the modification that causes this unusual shift in the C3 atom position has not been determined. However, the possibility of sulfation (by XPS) and phosphorylation (by $^{31}$P NMR and XPS) have been ruled out. The sample was analyzed at pH 9, but the unusual NMR signal remained, thus ruling out the possibility of a potential base-labile O-acetyl unit or an inter-residue lactone.

Figure 18:
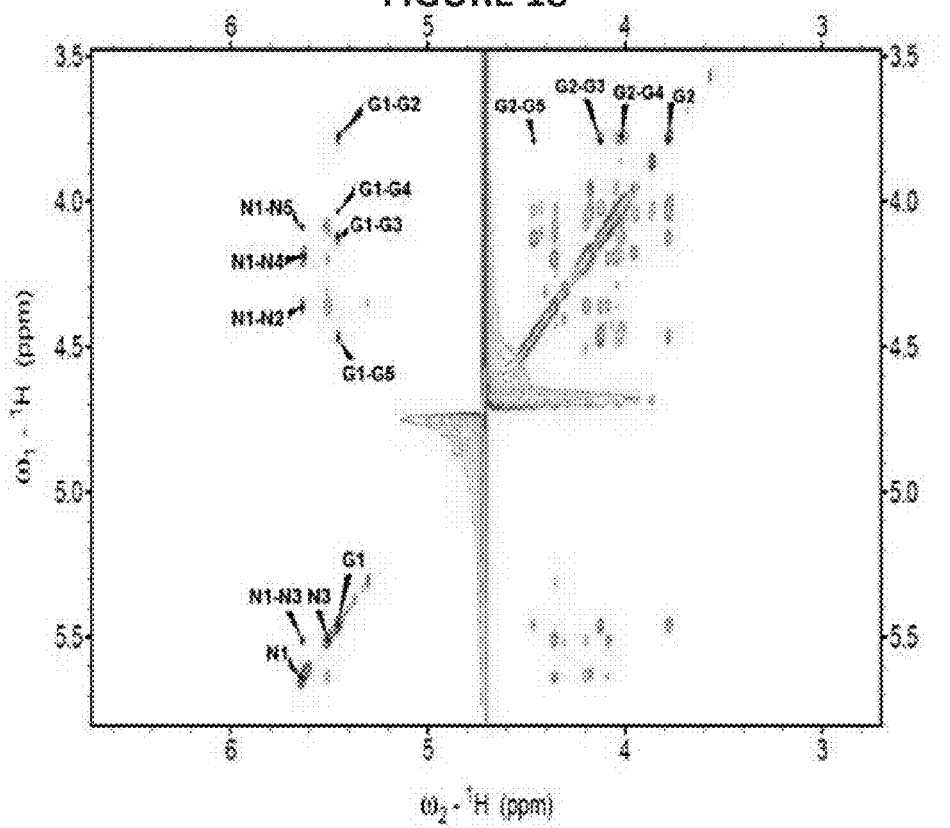
FIG. 18 contains two-dimensional $^1$H-$^1$H total correlation spectrum (TOCSY) of the native *Comamonas* polysaccharide at 328K. The spectrum was recorded at 800 MHz on a Bruker Avance II spectrometer. Mixing time 120 ms; delay time 1.5 seconds; acquisition time 0.852 s.
Figure 19:
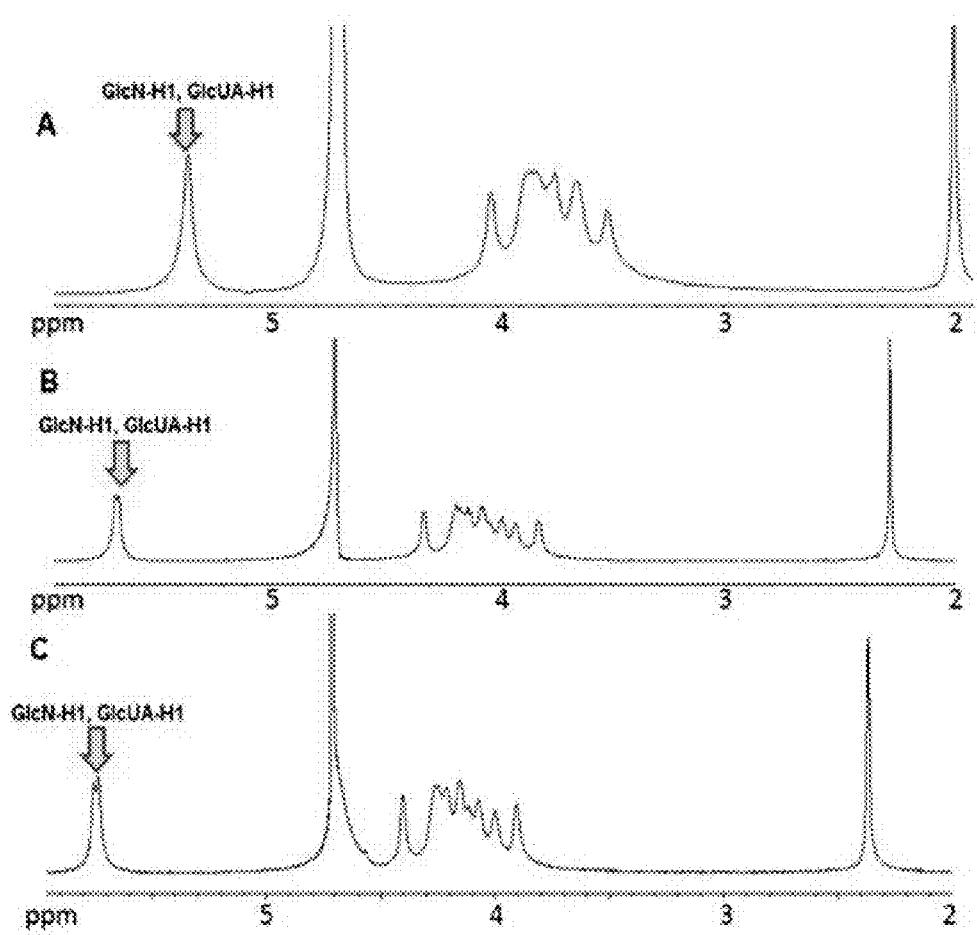
FIG. 19 contains $^1$H-NMR spectra of the synthetic *Comononas* polysaccharide at three different temperatures. 298K (A); 328K (B); 338K (C). The spectrum was recorded at 800 MHz on a Bruker Avance II spectrometer. Sweep width 20.55 ppm; acquisition time 2.650 s.

The synthetic polysaccharide was produced in vitro with pure precursors, UDP-GlcUA and UDP-GlcNAc. The $^1$H and $^{13}$C signals of the GlcUA residue in synthetic polysaccharide resonated at nearly identical chemical shift values as those observed for the native polysaccharides. The chemical shift values for the $^1$H and $^{13}$C signals for the GlcNAc residue were different for the two polysaccharides, particularly those at the 3-position. Moreover, overlap (even at 800 MHz field strength) between the proton at the 4-positions of both the GlcNAc and GlcUA residues in the synthetic polysaccharide initially made it impossible to definitively assign linkage positions. When the probe temperature was elevated up to 338 K, the GlcUA and GlcNAc anomeric signals could be partially separated (FIG. 18) but their linkage positions could still not be assigned by NOESY due to peak broadening. This problem was overcome by reducing the pD (the pH equivalent in deuterated water) of the synthetic polysaccharide sample from 6.9 to 3.6 (FIG. 19), allowing its structure to be definitely assigned as [-4-D-GlcUA-α1,4-D-GlcNAc-α1-]$_n$.

Discussion of Example 1

Glycosaminoglycans are hydrophilic polysaccharides that can play signaling, structural and protective roles in the human body. These properties make GAGs desirable molecules for therapeutics and tissue engineering. In the current Example, a bifunctional glycosaminoglycan synthase, CtTS, has been identified which is responsible, in part, for forming an extracellular polysaccharide in the bacteria *C. testosteroni* KF-1. The GAG backbone formed by the action of CtTS, testosteronan, consists of the same chemical composition as both heparosan and hyaluronan, but has distinct glycosidic linkages. Heparosan is [-4-D-GlcUA-β1,4-D-GlcNAc-α1-]$_n$ while hyaluronan is [-4-D-GlcUA-β1,3-D-GlcNAc-β1-]$_n$. The NMR studies have been able to confirm that this new GAG backbone has the structure [-4-D-GlcUA-α1,4-D-GlcNAc-α1-]$_n$. Therefore, the testosteronan backbone has identically configured GlcNAc units as heparosan; this observation probably explains why heparosan served as an acceptor for CtTS in vitro (as FIGS. 4 and 5 demonstrate), but not as efficiently as the native polymer found in *Comamonas* extracts.

Some bacterial pathogens utilize polysaccharide capsules with molecular structures similar or identical to their host organism to avoid host defenses such as antibodies, phagocytes, or complement. While the differences in the testosteronan structure may appear to be detrimental for the *Comamonas* microbe's strategy of molecular mimicry, some capsular glycans are not identical to host GAGs, but are still employed as virulence factors. Specific examples include: (i) heparosan of *P. multocida* Type D and *E. coli* K5 which is employed without sulfation or epimerization, and (ii) a fructosylated version of chondroitin is used by *E. coli* K4.

The glycosidic linkages of testosteronan are responsible for the polysaccharide's insensitivity to digestion by all GAG degrading enzymes tested thus far, but it should be susceptible to vertebrate lysosomal exoglycosidases. This property of testosteronan may prove useful for generating longer-lasting polysaccharides or biomaterials provided the molecule does not promote an immunological response in the human body.

Additionally, it is intriguing to consider the potential for this molecule to possess anticoagulant or anti-proliferative activity after chemical or enzymatic sulfation (Chen et al., 2005; Kuberan et al., 2003; Liu et al., 2010). This is due to the similar structure to that of heparosan, which is the precursor molecule to heparin, the highly sulfated, epimerized form of the same molecule. The only difference between heparosan and testosteronan is the change from β- to α-linkage configuration between the GlcUA and the GlcNAc residues. Therefore, any binding protein or factor that relies on this structure (or the conformation it assumes) may not interact with the testosteronan backbone as well as with that of heparosan, but conversely, other proteins that do not rely on this structure may be minimally affected. Furthermore, the novel structure may also interact better with a different subset of the proteins that bind or modify heparin or heparan sulfate polymers, resulting in higher potency molecules.

In some aspects, the alpha-linked glucuronic acid component of testosteronan may mimic the structure and/or the conformation of the iduronic acid (IdoUA; the epimerized form of GlcUA) component found in natural heparin and heparan sulfate. During production, the epimerization step in vitro is difficult to achieve in comparison to the sulfation steps (i.e., the epimerase enzyme is not robust, and its reaction is not driven forward by consumption of high energy phosphate bonds like sulfation or polymerization). In these cases, the production of testosteronan-containing polymers will be simplified compared to methods that require epimerized heparosan/heparan sulfate chains.

Materials and Methods of Example 1

Materials:
Wild-type *Comamonas testosteroni* KF-1 (DSM #14576) was obtained from the German collection of microorganisms and cell cultures (DSMZ). The strain was grown in chemically defined media (CDM) which is free of other polysaccharides and animal extracts (van De Rijn et al., 1980) (JRH Biosciences, Lenexa, Kans.). All reagents were from Sigma unless otherwise noted. Oligonucleotide primers were synthesized by Integrated DNA Technologies, Inc. (Coralville, Iowa).

Isolation and Analysis of Capsular Polysaccharide:
Wild-type *Comamonas testosteroni* KF-1 was grown in chemically defined medium (CDM) for 24 hours at 30° C. with shaking at 250 rpm. Cells were then removed from the culture by centrifugation. Spent media was treated with 0.1 μg/μl DNase/RNase for 2 hours at room temperature to degrade nucleic acids. The anionic polysaccharide fraction was precipitated by addition of 1% cetylpyridinium chloride (CPC) for 1 hour at room temperature. The pellet was collected by centrifugation (2,000×g for 60 minutes), washed with water, and resuspended in 1M NaCl. The solution was clarified by centrifugation, and the supernatant was ethanol precipitated (70% v/v final). The ethanol precipitation/1 M NaCl dissolution procedure was repeated twice, and then the pellet was washed with 70% ethanol. Finally, the pellet was resuspended in water, treated with 0.1 μg/μl DNase/RNase for 1 hour (20 mM Tris, pH 7.2, 1 mM MgCl$_2$) and extracted with CHCl$_3$ to remove proteins from the sample. This polysaccharide extract was further fractionated by anion exchange chromatography (HiTrap™ Q HP 1 ml column, GE LifeSciences, Uppsala, Sweden) using a 0.05-2 M ammonium formate gradient (1 ml/min for 93 minutes). The resulting fractions were analyzed by polyacrylamide gel electrophoresis (PAGE; 1×TBE, 6% acrylamide) with staining by Alcian Blue. Fractions containing the target polysaccharide (approximately 0.6-0.75 M ammonium formate) were pooled and lyophilized three times from water to remove the volatile ammonium formate. The polysaccharide pool was then treated with proteinase K (1 μg/μl enzyme, 50 mM NaOAc, pH 7.4, overnight at 30° C.) to destroy any contaminating proteins. In certain preparations, as noted, other HA-like polysaccharides were digested with ovine testicular hyaluronidase prior to proteinase K digestion. Digest reactions were $CHCl_3$ extracted to remove enzymes and exchanged via ultrafiltration into water (MICROCON® 30 kDa, 3× with 500 µl rinses). The retentate containing polysaccharide was purified on a PD-10 column (GE LifeSciences) to remove remaining low molecular weight contaminants. Briefly, the column was equilibrated, loaded and eluted as per manufacturer's instructions using 0.2 M ammonium formate buffer. The void volume fractions containing polysaccharide were pooled and lyophilized 3×. Uronic acid content was measured by the carbazole assay (Bitter et al., 1962) with glucuronic acid standard. Resulting polysaccharide was used for NMR and monosaccharide analysis.

For monosaccharide analysis, polysaccharides were subjected to acid hydrolysis; 30-100 µg of polysaccharide was incubated in 300 µl of 2 N trifluoroacetic acid (TFA) for 6 hours at 100° C. Finally, reactions were cooled to room temperature and dried in a rotary evaporator. Samples were dissolved in 50 µl of water, and 20 µl was subjected to anion exchange chromatography with pulsed amperometric detection on a Dionex DX600 instrument as described previously (DeAngelis et al., 2002) (Dionex, Inc., Sunnyvale, Calif.).

Cloning and Expression of Ct Synthase:

Genomic DNA was extracted from the wild-type Ct microbe grown in CDM media employing the ULTRACLEAN® Microbial DNA Sample Kit (MO BIO Laboratories, Inc., Carlsbad, Calif.) and used as a template for PCR using primers designed to amplify the predicted 1923 bp coding sequence (sense: ATGAGCGGCATGTTTAAGGTTGCCAATG (SEQ ID NO:3); antisense: TCATTTCACCATCATCTTTTTAATTCTGAG (SEQ ID NO:4)). The resulting PCR product was cloned into the pTrcHis-TOPO® vector (Invitrogen, Carlsbad, Calif.) according to manufacturer's instructions and transformed into E. coli TOP-10F' cells with selection on LB/ampicillin plates at 30° C. The plasmids of transformants were screened by restriction digest, and DNA plasmids positive for the correctly oriented insert were confirmed by sequencing both strands (Oklahoma Medical Research Foundation sequencing facility Oklahoma City, Okla.). Plasmid was then transformed into phage lysin-expressing freeze/thaw lysis E. coli XJa cells according to manufacturer's instructions (Zymo Research, Orange, Calif.). For protein production, cultures of E. coli XJa in Superior Broth (AthenaES, Baltimore, Md.) with ampicillin (50 µg/ml), carbinicillin (50 µg/ml) and L-arabinose (3.25 mM final; to induce the lysin enzyme) were grown at 30° C. Expression of target protein was induced by addition of isopropyl β-D-1-thiogalactopyranoside (IPTG, 0.2 mM final) at $OD_{600}$ 0.35. At 1 hour post-induction, growth was supplemented with fructose (12.8 mM final), and growth proceeded for approximately 16 hours before cells were harvested by centrifugation (3,000×g for 30 minutes at 4° C.). The cell pellet was resuspended in 50 mM Tris, pH 7.2, with protease inhibitors pepstatin, benzamidine, N—[N-(L-3-trans-carboxyoxirane-2-carbonyl)-L-leucyl]-agmatine, leupeptin) on ice and subjected to two freeze/thaw cycles to allow the phage lysin to degrade the cell walls. The lysates were then clarified by centrifugation (20,000×g for 30 minutes at 4° C.). Protein content was measured by the Bradford assay with a BSA standard (Thermo Fisher Scientific, Waltham, Mass.).

Glycosyltransferase Activity Assays:

Radiolabeled sugar incorporation assays (25 µl, 30 minutes at 22° C.) were performed using clarified lysates (60 µg total protein) in the presence of 0.05 mM UDP-GlcUA or UDP-GlcNAc as carrier with UDP-[$^3$H]GlcUA or UDP-[$^3$H]GlcNAc (0.1 µCi/assay) (NEN Perkin Elmer, Waltham, Mass.) with various unlabeled UDP-sugars (1 mM) or no second sugar as a negative control. The reaction buffer was 50 mM Tris, pH 7.2, 5 mM $MgCl_2$; these conditions were obtained after limited optimization trials. Certain reactions used acceptors (1 µg) to bypass de novo initiation, including HA, heparosan, or Ct polysaccharide (sonicated 10 minutes on ice to increase the number of termini).

Reactions were incubated at the indicated temperatures for the times noted, and then stopped with 2% final SDS and separated by descending paper chromatography (65:35 ethanol/1 M ammonium acetate buffer, Whatman 3MM paper). This method enabled the separation of GAG polysaccharides with greater than ~14 sugar units, which remain at the origin, from smaller oligomers and unincorporated nucleotide sugars that migrate down the strip. The origin of the strip was cut out and subjected to liquid scintillation counting (BIOSAFE™, RPI Corp, Mt. Prospect, Ill.).

Production of Synthetic Polysaccharide:

To produce larger amounts of the polysaccharide synthesized by the recombinant enzyme in vitro, 200 µl reactions were employed containing 10 mM each of unlabeled UDP-GlcNAc and UDP-GlcUA, 5 mM $MgCl_2$ and 50 mM Tris, pH 7.2, with 40 ng/µl heparosan tetrasaccharide as acceptor at 30° C. overnight using clarified lysates (3 mg/ml total protein). Synthetic polysaccharide was purified using the same methods as the native polysaccharide extract following (and including) the final $CHCl_3$ extraction, ultrafiltration and PD-10 column; the yield was 0.6 mg.

Digestion of Native and Synthetic Polysaccharide with GAG Degrading Enzymes:

Purified synthetic or native polysaccharide was treated with heparin lyase III from Pedobacter heparinus (previously Flavobacterium heparinum; kindly supplied by Jian Liu, Univ. of North Carolina) (0.2 mg/ml, 50 mM Tris, pH 7.2, at 30° C.) or ovine testicular hyaluronidase (0.4 mg/ml, 30 mM ammonium acetate, pH 5.5, at 30° C.) to help characterize the polysaccharide being produced by CtTS. Polysaccharides were analyzed post-treatment with either 6% PAGE (1×TBE) stained with Alcian Blue (Min, H. and Cowman, M. K. 1986) or 2% agarose gels (1×TAE) with Stains-all detection (Lee, H. G. and Cowman, M. K. 1994). Nearly monodisperse hyaluronan standards (Hyalose, LLC, Oklahoma City, Okla.) were used to estimate size (Jing et al., 2004). As a positive control for complete and specific digestion, internal standards of authentic hyaluronan or heparosan were employed as appropriate; the use of GAGs with molecular weights differing from the Ct polysaccharides allowed analysis of the test and standard samples in the same reaction and gel lane.

Acid Hydrolysis of Ct Native Polysaccharide Extract:

Purified native polysaccharide was partially fragmented with 1 M HCl at 95° C. for 15 minutes. The resulting hydrolyzed oligosaccharides were then analyzed by either thin layer chromatography (TLC) (silica plates with n-butanol, acetic acid, $H_2O$, 2:1:1 and staining by napthoresorcinol), or MALDI-ToF mass spectrometry. MALDI-ToF mass spectrometry was performed in reflector negative mode using an Ultraflex II instrument (Bruker Daltonics, Billerica, Mass.), with the matrix 6-aza-2-thiothymine (ATT) at a concentration of 5 mg/ml in 50% acetonitrile, 0.1% trifluoroacetic acid (TFA). HA oligosaccharides were employed as mass calibrants.

NMR Studies:

The native *Comamonas* and synthetic polysaccharides were analyzed by one-dimensional $^1$H and two-dimensional COSY, HMQC, TOCSY, NOESY, and ge-HMQC-TOCSY experiments to elucidate their structure. All NMR experiments were acquired on Bruker Avance II Ultrashield 600 MHz (14.1-Tesla) and 800 MHz (18.8-Tesla) NMR instruments equipped with an ultrasensitive HCN cryoprobe with a z-axis gradient. The spectra were mostly acquired at a probe temperature of 298 and 328K. Polysaccharides (approximately 0.5-1.5 mg) were dissolved in 0.4 ml of 99.996% deuterium oxide ($^2$H$_2$O, Sigma, St. Louis, Mo., USA) and freeze-dried to remove exchangeable protons. The residual water peak served as a reference (HOD, 4.76 ppm); typical silane standards were not employed due to water insolubility or lack of volatility that would interfere with subsequent analyses. The chemical shift of the water peak yields reliable chemical shift values for polysaccharides. For one-dimensional $^1$H-NMR spectra, sweep width of 20.5 ppm and acquisition time of 2.65 s were employed. For the $^1$H-$^1$H COSY, $^1$H-$^1$H TOCSY and NOESY spectra, 512 experiments resulting in 4096 data points for a spectral width of 10 ppm were measured. Proton-detected HMQC experiments used 10- and 78-ppm spectral widths in the $^1$H dimension and $^{13}$C dimension, respectively. A mixing time of 400 ms with 1.5 s relaxation delay and a mixing time of 50 ms with 1 s relaxation delay were used in NOESY and ge-HMQC-TOCSY experiments, respectively. The 2D NMR data sets were processed by Topspin version 2.1.4 and cross-peak assignments were carried out using an NMR assignment software Sparky (Goddard et al., 2001).

XPS Studies:

X-ray photoelectron spectroscopy measurements (1 mg sample/test) were carried out in a PHI 5400 instrument (Physical Electronics, Chanhassen, Minn.) with a 200 W Al Kalpha mono probe beam. The spectrometer was configured to operate at high resolution with pass energy of 117.40 eV.

Example 2: Polymer Grafting of Testosteronan onto Acceptors Using CtTS

Figure 21:
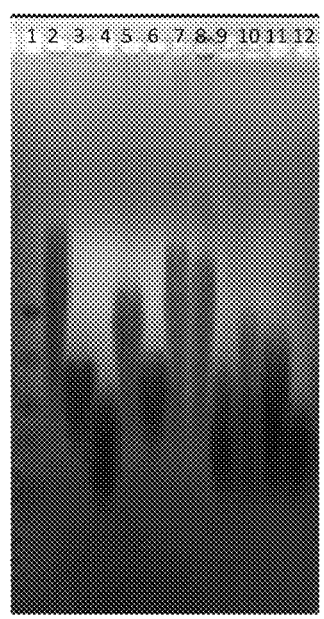
FIG. 21 illustrates polymer grafting onto various small acceptor molecules utilizing testosteronan synthase. The recombinant *Comononas testosteroni* synthase was incubated with both UDP-sugars and various acceptors (note: monosaccharides or glycosides first subjected to two extension steps via CtTS enzyme before adding both UDP sugars) OR 'no acceptor' in reaction buffer. The reactions were then subjected to agarose gel analysis with Stains-all dye detection. From left to right, the lanes are as follows: (1) HA LoLadder standard; (2) 'no acceptor' (de novo synthesis); (3) p-Nitrophenyl-β-D-glucuronide (15 µM); (4) p-Nitrophenyl-β-D-glucuronide (30 µM); (5) GlcUA (15 µM); (6) GlcUA (30 µM); (7) GlcNAc (15 µM); (8) GlcNAc (30 µM); (9) AFA=GlcUA-fluorescein-GlcUA (15 µM); (10) AFA (30 µM); (11) Hep4=base de-acetylated, nitrous acid, & reduced heparosan tetrasaccharide (15 µM); and (12) Hep4 (30 µM). Size control (i.e., differences in molecular weight between 15 and 30 µM) is noted with certain acceptors.

The recombinant *Comononas testosteroni* synthase was incubated with both UDP-sugars and various acceptors OR 'no acceptor' in reaction buffer. The reactions were then subjected to agarose gel analysis with Stains-all dye detection, as shown in FIG. 21. From left to right in FIG. 21, the lanes are listed below in Table 3.

TABLE 3

| Lane | Acceptor |
|---|---|
| 1 | HA LoLadder standard |
| 2 | 'no acceptor' (de novo synthesis) |
| 3 | p-Nitrophenyl-β-D-glucuronide (15 µM) |
| 4 | p-Nitrophenyl-β-D-glucuronide (30 µM) |
| 5 | GlcUA (15 µM) |
| 6 | GlcUA (30 µM) |
| 7 | GlcNAc (15 µM) |
| 8 | GlcNAc (30 µM) |
| 9 | AFA = GlcUA-fluorescein-GlcUA (15 µM) |
| 10 | AFA (30 µM) |
| 11 | Hep4 = base de-acetylated, nitrous acid, & reduced heparosan tetrasaccharide (15 µM) |
| 12 | Hep4 (30 µM) |

For all acceptors except Hep4 and AFA, the final acceptor was produced in situ before elongation by extending stepwise with the next two appropriate UDP-sugars. For example, GlcUA was extended first with UDP-GlcNAc, then UDP-GlcUA (making a trisaccharide) before the complete polymerization reaction components (i.e., a mixture of many equivalents of UDP-GlcUA and UDP-GlcNAc together to allow the production of long polymer chains) were added. Two different concentrations of the acceptor were added (either 15 or 30 µM as noted) to test the effect of stoichiometric size control.

As noted by the smaller molecular weight (MW) products that could be size-controlled (i.e., less acceptor makes longer chains while more acceptor makes shorter chains), the p-Nitrophenyl-D-glucuronide and the GlcUA monosaccharide allowed efficient size control (i.e., similar to Hep4 and AFA products), while the GlcNAc monosaccharide did not (i.e., a high MW product similar to the 'no acceptor' lane was observed).

Thus, in accordance with the presently disclosed and claimed inventive concept(s), there has been provided a novel heparosan analog, testosteronan, as well as a novel testosteronan synthase, and methods of producing and using same, that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Arda B et al. 2003. APMIS, 111:474-476.
Bitter T, Muir H M. 1962. Analytical biochemistry, 4:330-334.
Bossier P, Verstraete W. 1996. Appl Environ Microbiol, 62:2687-2691.
Cantarel B L, et al. 2009. Nucleic Acids Res, 37:D233-238.
Chen J, et al. 2005. J Biol Chem, 280:42817-42825.
DeAngelis P L. 1996. Biochemistry, 35:9768-9771.
DeAngelis P L, et al. 1998. *J Biol Chem*, 273:8454-8458.
DeAngelis P L. 1999. Cell Mol Life Sci, 56:670-682.
DeAngelis P L. 2002. Glycobiology, 12:9R-16R.
DeAngelis P L, et al. 2002. Carbohydr Res, 337:1547-1552.
DeAngelis P L, et al. 1997. Science, 278:1800-1803.
DeAngelis P L, Padgett-McCue A J. 2000. J Biol Chem, 275:24124-24129.
DeAngelis P L, et al. 1993. J Biol Chem, 268:19181-19184.
DeAngelis P L, White C L. 2002. J Biol Chem, 277:7209-7213.
DeAngelis P L, White C L. 2004. J Bacteriol, 186:8529-8532.
Dias F F, Bhat J V. 1964. Appl Microbiol, 12:412-417.
Drummond A, et al. 2010. Geneious 4.7.6. Auckland, New Zealand.
Goddard T D, Kneller D G. 2001. SPARKY. 3rd ed. San Francisco (Calif.): University of California.
Gul M, et al. 2007. Short communication. Acta Microbiol Immunol Hung, 54:317-321.
Horinouchi M, et al. 2010. J Steroid Biochem Mol Biol, 122:253-263.
Jin L, et al. 2008. J Forensic Sci, 53:1198-1199.

Jing W, DeAngelis P L. 2000. Glycobiology, 10:883-889.
Jing W, DeAngelis P L. 2004. J Biol Chem, 279:42345-42349.
Jing W, et al. 2006. Anal Biochem, 355:183-188.
Kuberan B, et al. 2003. J Am Chem Soc, 125:12424-12425.
Lee H G, Cowman M K. 1994. Analytical biochemistry, 219:278-287.
Linares M, et al. 2008. J Steroid Biochem Mol Biol, 112:145-150.
Liu R, et al. 2010. J Biol Chem, 285:34240-34249.
Ma Y-F, et al. 2009. Appl Environ Microbiol, 75:6812-6819.
Min H, Cowman M K. 1986. Anal Biochem, 155:275-285.
Ninomiya T, et al. 2002. J Biol Chem, 277:21567-21575.
Otto, N J, et al. 2011. Glycobiology, 21:1331-40.
Otto, N J, et al. 2012. J Biol Chem, January 10 Epub (PMID:22235128)
Pummill, P E, et al. 2003. J Biol. Chem 278:19808-14.
Reddy A K, et al. 2009. J Med Microbiol, 58:374-375.
Schleheck D, et al. 2004. Appl Environ Microbiol, 70:4053-4063.
Schleheck D, et al. 2010. Appl Environ Microbiol, 76:196-202.
Sismey-Ragatz A E, et al. 2007. J Biol Chem, 282:28321-28327.
van De Rijn I, Kessler R E. 1980. Infect Immun, 27:444-448.
Weigel P H, DeAngelis P L. 2007. J Biol Chem, 282:36777-36781.
Weïwer M, et al. 2008. J Org Chem, 73:7631-7637.

What is claimed is:

1. A method of producing a polymer, at least a portion of which has the repeat structure [4-D-glucuronic acid-α1,4-D-N-acetylglucosamine-α1-]$_n$ ([-4-D-GlcUA-α1,4-D-GlcNAc-α1-]$_n$), the method comprising the steps of:
   culturing a recombinant host cell that comprises a nucleic acid encoding an enzymatically active testosteronan synthase, wherein the testosteronan synthase is a single protein that is a dual-action catalyst that utilizes UDP-GlcUA and UDP-GlcNAc to synthesize a polymer having the repeat structure [-4-D-GlcUA-α1,4-D-GlcNAc-α1-]$_n$, wherein the recombinant host cell is cultured under conditions that allow for the production of the enzymatically active testosteronan synthase and under conditions that allow the testosteronan synthase to produce the polymer having the repeat structure [-4-D-GlcUA-α1,4-D-GlcNAc-α1-]$_n$, wherein the recombinant host cell is cultured in the presence of at least one UDP-sugar or comprises nucleic acids encoding enzymes which catalyze the synthesis of at least one UDP-sugar, and wherein the nucleotide sequence encoding the enzymatically active testosteronan synthase is defined as:
   (a) the nucleotide sequence of SEQ ID NO: 2;
   (b) a nucleotide sequence encoding the amino acid sequence of SEQ ID NO: 1;
   (c) a nucleotide sequence encoding an amino acid sequence having up to 30 amino acid insertions, deletions, and/or substitutions when compared to SEQ ID NO: 1; and/or
   (d) a nucleotide sequence encoding an amino acid sequence having up to 25 amino acid insertions, deletions, and/or substitutions when compared to SEQ ID NO:1; and
   isolating the polymer having the repeat structure [-4-D-GlcUA-α1,4-D-GlcNAc-α1-]$_n$.

2. The method of claim 1, wherein the recombinant host cell comprises nucleic acids encoding enzymes which catalyze the synthesis of UDP-GlcUA and UDP-GlcNAc.

3. The method of claim 1, further comprising the step of supplying UDP-GlcUA and UDP-GlcNAc to the recombinant host cell.

4. The method of claim 1, wherein the isolated polymer is substantially monodisperse in size and has a polydispersity value in a range of from 1.0 to 1.5.

5. The method of claim 1, wherein the recombinant host cell is a prokaryotic cell.

6. The method of claim 1, wherein the recombinant host cell is a eukaryotic cell.

7. The method of claim 1, wherein the recombinant host cell further comprises:
   a nucleic acid encoding an enzymatically active UDP-glucose dehydrogenase; and/or
   a nucleic acid encoding an enzymatically active UDP-glucose pyrophosphorylase.

8. A method of producing a polymer, at least a portion of which has the repeat [-4-D-GlcUA-α1,4-D-GlcNAc-α1-]$_n$, the method comprising the steps of:
   culturing a recombinant host cell in a culture medium under conditions that allow for the production of an enzymatically active testosteronan synthase and under conditions that allow the testosteronan synthase to produce the polymer having the repeat structure [-4-D-GlcUA-α1,4-D-GlcNAc-α1-]$_n$, wherein the recombinant host cell comprises a recombinant vector comprising a nucleotide sequence encoding an enzymatically active testosteronan synthase, wherein the testosteronan synthase is a single protein that is a dual-action catalyst that utilizes UDP-GlcUA and UDP-GlcNAc to synthesize a polymer having the repeat structure [-4-D-GlcUA-α1,4-D-GlcNAc-α1-]$_n$, wherein the recombinant host cell is cultured in the presence of at least one UDP-sugar or comprises nucleic acids encoding enzymes which catalyze the synthesis of at least one UDP-sugar, and wherein the nucleotide sequence encoding the enzymatically active testosteronan synthase is defined as:
   (a) the nucleotide sequence of SEQ ID NO: 2;
   (b) a nucleotide sequence encoding the amino acid sequence of SEQ ID NO: 1; and/or
   (c) a nucleotide sequence encoding an amino acid sequence having up to 25 amino acid insertions, deletions, and/or substitutions when compared to SEQ ID NO:1; and isolating the polymer having the repeat structure [-4-D-GlcUA-α1,4-D-GlcNAc-α1-]$_n$.

9. The method of claim 8, wherein the polymer is isolated from the culture medium.

10. The method of claim 8, wherein the recombinant vector further comprises a nucleic acid encoding an enzymatically active UDP-glucose dehydrogenase and/or a nucleic acid encoding an enzymatically active UDP-glucose pyrophosphorylase.

11. The method of claim 8, wherein the recombinant vector further comprises nucleic acids encoding enzymes which catalyze the synthesis of UDP-GlcUA and UDP-GlcNAc.

12. The method of claim 8, further comprising the step of supplying UDP-GlcUA and UDP-GlcNAc to the recombinant host cell.

13. The method of claim 8, wherein the nucleotide sequence of (c) encodes an amino acid sequence having up to 15 amino acid insertions, deletions, and/or substitutions when compared to SEQ ID NO:1.

14. The method of claim 8, wherein the nucleotide sequence of (c) encodes an amino acid sequence having up to 10 amino acid insertions, deletions, and/or substitutions when compared to SEQ ID NO:1.

15. The method of claim 8, wherein the nucleotide sequence encoding the enzymatically active testosteronan synthase is defined as:
   (a) the nucleotide sequence of SEQ ID NO:2; and/or
   (b) a nucleotide sequence encoding the amino acid sequence of SEQ ID NO:1.

\* \* \* \* \*

```
SEQUENCE LISTING

<160> NUMBER OF SEQ ID NOS: 6

<210> SEQ ID NO 1
<211> LENGTH: 640
<212> TYPE: PRT
<213> ORGANISM: Comomonas testosteroni

<400> SEQUENCE: 1

Met Ser Gly Met Phe Lys Val Ala Asn Asp Phe Phe Ser Asn Gly Asn
1               5                   10                  15

Phe Glu Lys Ala Ile Glu Arg Tyr Glu Glu Ile Ile Phe Lys Tyr Pro
            20                  25                  30

Gly Leu Thr Glu Phe Ala Ser Gly Asn Leu Ala Leu Ala Arg Arg Lys
        35                  40                  45

Leu Gly Glu Arg Gln Glu Asn Lys Ser Lys Ser Leu Val Asn Ala Ser
    50                  55                  60

Lys Ile Ser Glu Ser Ile Phe Val Gly Ile Ala Ala Ile Pro Glu Arg
65                  70                  75                  80

Ala Lys Ala Leu Glu Lys Thr Ile Glu Ser Leu Leu Pro Gln Val Glu
                85                  90                  95

Lys Ile Gly Val Tyr Leu Asn Gly Trp Lys Glu Val Pro Asp Tyr Leu
            100                 105                 110

Lys Asn Glu Lys Ile Leu Val Glu Gly Phe Gly Lys Glu Asp Leu Gly
        115                 120                 125

Asp Val Gly Lys Phe Phe Trp Val Asp Gln His Asp Gly Ile Tyr Phe
    130                 135                 140

Ser Cys Asp Asp Asp Leu Ile Tyr Pro Lys Asp Tyr Val Asp Arg Thr
145                 150                 155                 160

Val Glu Lys Leu Lys Glu Lys Asn Tyr Lys Ala Ala Ile Gly Trp His
                165                 170                 175

Gly Ser Leu Leu Arg Asp Asn Phe Ser Thr Tyr Tyr Asp Lys Asn Ser
            180                 185                 190

Arg Arg Val Phe Val Phe Ser Ala His Arg Pro Trp Asp Thr Pro Val
        195                 200                 205

His Ile Leu Gly Thr Gly Cys Ser Ala Phe His Thr Lys Phe Leu Lys
    210                 215                 220

Ile Lys Lys Ser Asp Phe Leu His Pro Asn Met Ala Asp Ile Phe Phe
225                 230                 235                 240

Ser Ile Lys Gly Gln Glu Gln Lys Ile Pro Phe Ile Val Leu Ala His
                245                 250                 255

Glu Lys Asp Glu Ile Thr Glu Phe Val Gly Ala Lys Glu Ser Ser Ile
            260                 265                 270
```

Tyr Ser His Ser Gln Ala Asn Val Glu Ser Lys Lys Asn Thr His Asp
         275                 280                 285

Leu Gln Asn Gly Phe Val Met Lys Asn Met Pro Trp Val Met Asn Asp
    290                 295                 300

Val Glu Ser Leu Ser Val Leu Ile Val Gly Arg Phe Glu Asn Tyr Ser
305                 310                 315                 320

Lys Gly Gly Ile Tyr Lys Ser Cys His Leu Ile Lys Glu His Leu Ser
                325                 330                 335

Ala Leu Gly His Asp Val Asp Ile His Asp Thr Gln Asn Pro Phe Ala
                340                 345                 350

Lys Ala Leu Glu Lys Lys Tyr Asp Leu Cys Trp Ile Tyr Pro Gly Asp
            355                 360                 365

Pro Glu Arg Pro Asp Phe Ser Ser Val Glu Asp Lys Ile Tyr Glu Leu
    370                 375                 380

Lys Ser Arg Gly Ile Pro Val Ile Val Asn Leu Ser Tyr Leu Tyr Ser
385                 390                 395                 400

Glu Asp Arg Thr Ile Trp Ile Arg Asn Lys Ile Arg Asp Leu Asn Ala
                405                 410                 415

Lys Gly Thr Thr Pro Val Leu Gly Ala Val Phe Thr Glu Thr Ala Ala
            420                 425                 430

Asn Asp Pro Leu Leu Lys Asp Val Arg Asp Tyr Ile Cys Val Val Pro
    435                 440                 445

Lys Thr Ile Leu Pro Thr Pro Cys Glu Arg Tyr Tyr Glu Phe Gly Glu
450                 455                 460

Arg Glu Gly Ile Cys Leu Gly Asp Ala Thr Lys Leu Gly Asn Ala Lys
465                 470                 475                 480

Val Ile Gly Gly Asn Val Asn Asn Trp Ile Asp Ala Ile His Asn Arg
                485                 490                 495

Leu Pro His Val Asn Leu Tyr Ala Tyr Lys Gln Tyr Gln Gly Asn Asn
                500                 505                 510

Pro His Pro Lys Ile Lys Tyr Ala Pro His Met Lys Glu Asn Phe Gly
            515                 520                 525

Asp Trp Leu Ala Gln Arg Arg Ile Phe Ile Cys Leu Asn Val His Leu
    530                 535                 540

Thr Phe Glu Met Val Ala Cys Glu Ala Gln Ser Tyr Gly Thr Pro Val
545                 550                 555                 560

Ile Tyr Arg His Met Pro His Ser Leu Ser Glu Tyr Ile Ser Ala Thr
                565                 570                 575

Gly Phe Ala Thr Arg Ser Pro Asp Glu Met Ala Glu Met Val Ala Trp
            580                 585                 590

Leu Tyr Asn Asn Asn Lys Ala Trp Asn Lys Met Ser Gln Ala Ser Leu
    595                 600                 605

Asn Asn Gly Lys Ala Asn Asn Val Asn Leu Leu Asp Ser Ser Leu Glu
610                 615                 620

Gly Tyr Leu Arg Leu Ala Ile Leu Arg Ile Lys Lys Met Met Val Lys
625                 630                 635                 640

<210> SEQ ID NO 2
<211> LENGTH: 1923
<212> TYPE: DNA
<213> ORGANISM: Comomonas testosteroni

<400> SEQUENCE: 2
atgagtggaa tgtttaaggt tgccaatgat tttttctcta acggtaattt tgaaaaagca        60

```
attgaacgtt atgaggaaat aatttttaag tatccaggct tgacagagtt tgcgtcaggg      120
aatttagcgc tggcaagaag aaaactagga gagcgccaag aaaataaatc taaatcattg      180
gtgaatgctt ccaagatatc tgagagtatt tttgtaggta tagcagctat accagaacgc      240
gcgaaagctt tagagaaaac tattgagtct ttattgcctc aggtagaaaa ataggggtt       300 tacttaaacg gttggaagga agtcccagat tacttgaaga atgagaaaat ccttgtagag      360
ggattcggca aagaagacct gggagacgtg ggtaagtttt tttgggtgga tcagcatgat      420
ggaatctatt tctcatgtga tgacgactta atctatccaa aggactatgt tgatagaaca      480
gttgaaaagt taaagagaa aaattacaaa gctgcaattg gctggcatgg ttctctattg       540
agagataatt ttagtactta ttacgataag aattctcgac gtgttttttgt ttttttctgca    600 catcgtccat gggatacgcc tgtacatatt ctaggtacag gatgctcagc gttccatact      660
aagttcttaa agataaagaa gtctgatttt ctgcatccaa atatggcgga tatatttttc      720
tccattaaag ggcaggaaca aaaaatacct tttattgtct tggcgcatga aaaagatgaa      780
ataacagagt ttgttggggc taaggaaagc tctatttact cgcattctca ggcgaatgtg      840
gaatcgaaaa aaaatacccca tgatttgcaa aatggttttg taatgaaaaa catgccatgg     900
gtcatgaatg atgtcgagtc tctatctgtt ttgatagttg gtagatttga aaattatagt      960
aaaggtggga tctataagtc atgccatctt attaaagagc atctgtcggc actgggtcat     1020
gatgttgata ttcatgatac tcaaaatcca ttcgccaagg cgttagagaa aaaatatgat    1080
ctgtgttgga tacccagg tgatcctgag cgaccagatt tttctagtgt tgaagataaa      1140
atttatgaac tgaagtcaag gggtattccg gtaatcgtta atctctctta tttgtattct    1200
gaagatcgaa ccatatggat tcgaaataaa atacgagatt tgaatgcgaa aggaactact    1260
cctgtacttg gagctgtgtt tacagaaact gccgcaaatg atccgctgct aaaagatgtg   1320
agagactata tttgcgtcgt tcctaagacg atactaccta caccttgtga aaggtattat   1380
gagtttggtg agcgagaggg tatatgtttg ggggatgcaa cgaaactcgg gaatgctaaa    1440
gttataggcg gtaatgttaa taattggatt gatgcaattc acaatagact tcctcatgtc   1500
aatctttatg catacaagca gtatcaaggt aataacccac atccaaagat taaatatgct    1560
ccacatatga aagagaattt tggtgattgg ttggcgcaac gtaggatatt tatctgtttg   1620
aacgttcatt taacatttga gatggtggcg tgcgaggcgc aaagttacgg tacacctgtg   1680
atttatagac atatgccgca ctccttgagt gagtatatct ctgctacggg gtttgcaact  1740
cggtcacctg atgaaatggc tgaaatggtg gcatggttat ataataataa caaggcgtgg   1800
aataagatga gtcaagcttc tctaaataat gggaaggcta ataatgttaa tttattagac    1860
tcctctcttg aggggtattt gagattggct attctcagaa ttaaaaagat gatggtgaaa   1920
tga                                                                    1923
```

<210> SEQ ID NO 3
<211> LENGTH: 28
<212> TYPE: DNA
<213> ORGANISM: Comomonas testosteroni

<400> SEQUENCE: 3

```
atgagcggca tgtttaaggt tgccaatg                                           28
```

<210> SEQ ID NO 4
<211> LENGTH: 30
<212> TYPE: DNA

<213> ORGANISM: Comomonas testosteroni

<400> SEQUENCE: 4
tcatttcacc atcatctttt taattctgag                    30

<210> SEQ ID NO 5
<211> LENGTH: 617
<212> TYPE: PRT
<213> ORGANISM: Pasteurella multocida

<400> SEQUENCE: 5

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350
```

```
Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Thr Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615

<210> SEQ ID NO 6
<211> LENGTH: 651
<212> TYPE: PRT
<213> ORGANISM: Pasteurella multocida

<400> SEQUENCE: 6

Met Lys Gly Lys Lys Glu Met Thr Gln Ile Gln Ile Ala Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Lys Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
```

```
            100                 105                 110
Lys Ser Asp Leu Gly Leu Val Lys Glu Thr Asn Ser Ala Asn Pro Leu
        115                 120                 125

Val Ser Ile Ile Met Thr Ser His Asn Thr Ala Gln Phe Ile Glu Ala
        130                 135                 140

Ser Ile Asn Ser Leu Leu Leu Gln Thr Tyr Lys Asn Ile Glu Ile Ile
145                 150                 155                 160

Ile Val Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
                180                 185                 190

Leu Gly Thr Tyr Phe Ala Lys Asn Thr Gly Ile Leu Lys Ser Lys Gly
            195                 200                 205

Asp Ile Ile Phe Phe Gln Asp Ser Asp Val Cys His His Glu Arg
        210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Lys Lys Val Phe Gln Glu Ile Gly Phe Phe Asn Cys Thr Thr Lys
            275                 280                 285

Gly Ser Asp Asp Glu Phe Phe His Arg Ile Ala Lys Tyr Tyr Gly Lys
        290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
        370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Gln Arg Ile Gly Ile Leu Lys Asn
                405                 410                 415

Gln Cys Asp His Phe His Ile Tyr Leu Asp Gly Tyr Val Glu Ile Pro
        420                 425                 430

Asp Phe Ile Lys Asn Leu Gly Asn Lys Ala Thr Val His Cys Lys
        435                 440                 445

Asp Lys Asp Asn Ser Ile Arg Asp Asn Gly Lys Phe Ile Leu Leu Glu
    450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525
```

```
Phe Tyr Lys Pro Leu Glu Lys Asp Lys Ala Val Asn Val Leu Gly Thr
        530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
                580                 585                 590

Leu Thr Glu Asp Asn Arg Asp Ser Glu Thr Leu Tyr His Gln Tyr Arg
            595                 600                 605

Asp Asn Asp Glu Gln Gln Thr Gln Leu Ile Met Glu Asn Gly Pro Trp
        610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
                645                 650
```

UNITED STATES PATENT AND TRADEMARK OFFICE
CERTIFICATE OF CORRECTION

PATENT NO. : 10,273,517 B2
APPLICATION NO. : 15/594860
DATED : April 30, 2019
INVENTOR(S) : Paul L. DeAngelis and Nigel J. Otto It is certified that error appears in the above-identified patent and that said Letters Patent is hereby corrected as shown below:

In the Specification

Column 4, Line 62: Delete "*Comononas*" and replace with -- *Comamonas* --

Column 4, Line 67: Delete "*Comomonas*" and replace with -- *Comamonas* --

Column 13, Line 16: Delete "Tris-HCI" and replace with -- Tris-HCl --

Column 14, Line 15: Delete "lichemformis" and replace with -- licheniformis --

Column 17, Line 13: Delete "xIHAS1" and replace with -- xlHAS1 --

Column 29, Line 36: Delete "A1" and replace with -- Al --

Signed and Sealed this
Twenty-fifth Day of June, 2019

Andrei Iancu
*Director of the United States Patent and Trademark Office*